US008761898B2

(12) United States Patent
Jaroch et al.

(10) Patent No.: US 8,761,898 B2
(45) Date of Patent: Jun. 24, 2014

(54) FLEXIBLE NEURAL PROBE FOR MAGNETIC INSERTION

(75) Inventors: David Benjamin Jaroch, Lafayette, IN (US); Pedro Irazoqui, Lafayette, IN (US); Jenna Leigh Rickus, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/117,825

(22) Filed: May 27, 2011

(65) Prior Publication Data

US 2011/0257715 A1 Oct. 20, 2011

Related U.S. Application Data

(63) Continuation of application No. PCT/US2009/066075, filed on Nov. 30, 2009.

(60) Provisional application No. 61/118,628, filed on Nov. 30, 2008.

(51) Int. Cl.
*A61N 1/00* (2006.01)

(52) U.S. Cl.
USPC ........... 607/116; 128/897; 600/585; 606/129; 606/130

(58) Field of Classification Search
USPC ................... 606/129, 130; 600/585; 128/897
See application file for complete search history.

(56) References Cited

U.S. PATENT DOCUMENTS

| 5,833,600 A | * | 11/1998 | Young ........................ 600/300 |
| 2005/0159743 A1 | * | 7/2005 | Edwards et al. ............... 606/41 |
| 2007/0021730 A1 | * | 1/2007 | Flaherty et al. ............... 604/506 |

OTHER PUBLICATIONS

Bernatchez, Stephanie; Patrick Parks; Donald Gibbons; "Interaction of macrophages with fibrous materials in vitro"; Elsevier, Biomaterials vol. 17 No. 21; Jan. 24, 1996; pp. 2077-2086; Great Britain.

Bjornsson, C S; S J Oh; Y A Al-Kofani; Y J Lim; K L Smith; J N Turner; S De; B Roysam; W Shain; S J Kim; "Effects of insertion conditions on tissue strain and vascular damage during neuroprosthetic device insertion"; Journal of Neural Engineering; Institute of Physics Publishing; J. Neural Eng. 3; Jun. 21, 2006; pp. 1969-207; UK.

Bresie, D A; J A Andrews; "Design of a Reluctance Accelerator"; IEEE Transactions on Magnetics, vol. 27, No. 1; Jan. 1991; pp. 623-627; Austin, TX.

Cheung, Karen; Phillippe Renaud; Heikki Tanila; Kaj Djupsund; "Flexible polyimide microelectrode array for in vivo recordings and current source density analysis"; Biosensors & Bioelectronics 22; Elsevier; Oct. 5, 2006; pp. 1783-1790.

(Continued)

*Primary Examiner* — Michael Kahelin
*Assistant Examiner* — Mallika D Fairchild
(74) *Attorney, Agent, or Firm* — Maginot Moore & Beck LLP

(57) ABSTRACT

A neural probe deployment system comprising a magnetic probe, a magnetic field generator acting on the magnetic probe, a first guiding tube disposed on a first side of the magnetic field generator, wherein the magnetic probe is loaded inside the first guiding tube, and a second guiding tube disposed on a second side of the magnetic field generator, wherein activation of the magnetic field generator propels the magnetic probe from the first guiding tube through the second guiding tube, thereby deploying the magnetic probe.

20 Claims, 13 Drawing Sheets

(56) References Cited

OTHER PUBLICATIONS

Cho, Hyoung; Chong Ahn; "Microscale resin-bonded permanent magnets for magnetic micro-electro-mechanical systems applications"; American Institute of Physics, Journal of Applied Physics 93 No. 10, 8674; Nov. 15, 2002.

Cogan, Stuart; "Neural Stimulation and Recording Electrodes"; Annual Review of Biomedical Engineering, 2008 10; Apr. 22, 2008; pp. 275-309.

Das, R; D Gandhi; S Krishnan; L Saggere; P J Rousche; "A Benchtop System to Assess Cortical Neural Interface Micromechanics"; IEEE Transactions on Biomedical Engineering, vol. 54, No. 6; Jun. 2007; pp. 1089-1096.

Delille, Remi; Mario Urdaneta; "Benchtop Polymer MEMS; Journal of Microelectromechanical Systems", vol. 15, No. 5; pp. 1108-1120; Oct. 1996.

Dobelle, WM H; "Artificial Vision for the Blind by Connecting a Television Camera to the Visual Cortex"; ASAIO Journal 2000; 46:3-9; Dec. 1, 1999; New York, NY.

Edell, David; Vo Van Toi; Vincent McNeil; Lloyd Clark; "Factors Influencing the Biocompatibility of Insertable Silicon Microshafts in Cerebral Cortex"; IEEE Transactions on Biomedical Engineering, vol. 39, No. 6; Jun. 1992; pp. 635-643.

Farshad, M; Andre Benine; "Magnetoactive Elastomer Composites"; Polymer Testing Elsevier Ltd.; Jul. 18, 2003; pp. 347-353; Dubendorf, Switzerland.

Gerstein, George; Benoit Mandelbrot; "Random Walk Models for the Spike Activity of a Single Neuron"; Center for Communication Sciences, Research Laboratory of Electronics, Massachusetts Institute of Technology, Cambridge, Massachusetts; Harvard University, Cambridge, Massachusetts; and IBM Thomas J. Watson Research Center, Yorktown Heights, NY; pp. 41-67; Mar. 19, 1963.

Gilletti, Aaron; Jit Muthuswamy; "Brain micromotion around implants in the rodent somatosensory cortex"; Institute of Physics Publishing, Journal Neural Engineering 3; pp. 189-195; Jun. 7, 2006.

Gillies, G T; R C Ritter,;W C Broaddus; M S Grady; M A Howard; et al; "Magnetic manipulation instrumentation for medical physics research"; American Institute of Physicals, Review of Scientific Instruments vol. 65 No. 3, Mar. 1994, pp. 533-562; Dec. 13, 1993.

Grady, M Sean, MD; Matthew Howard III MD, William Broaddus MD, PhD, Janelle Molloy MS, Rogers Ritter, PhD, Elizabeth Quate MS; George Gillies PhD; "Magnetic Sterotaxis: A Technique to Deliver Stereotactic Hyperthermia"; Neurosurgery, vol. 27, No. 6 1990; pp. 1010-1016.

Grady, M S; M A Howard III; J A Molloy; R C Ritter; E G Quate; G T Gillies; "Nonlinear magnetic stereotaxis: Three-dimensional, in vivo remote magnetic manipulation of a small object in canine brain"; 1990 Am. Assoc. Phys. Med., Med. Phys. 17 (3), May/Jun 1990; pp. 405-415.

Grady, M S; M A Howard III; J A Molloy; R C Ritter; E G Quate; G T Gillies; "Preliminary experimental investigation of in vivo magnetic manipulation: Results and potential application in hyperthermia"; 1989 Am. Assoc. Phys. Med., Med. Phys. 16(2), Mar./Apr. 1989; pp. 263-272.

He, Wei; Ravi Bellamkonda; "Nanoscale neuro-integrative coatings for neural implants"; Biomaterials 26 (2005); 2004 Elsevier Ltd.; pp. 2983-2990.

He, Wei; George McCONNELL; Thomas Schneider; Ravi Bellamkonda; "A Novel Anti-inflammatory Surface for Neural Electrodes"; 2007 Wiley-VCH Verlag GmbH & Co. KGaA, Weinheim; Advanced Materials 2007, 19; pp. 3529-3533.

Hochberg, Leigh; Mijail Serruya; Gerhard Friehs; Jon Mukand; Maryam Saleh; Abraham Caplan; Almut Branner; David Chen, Richard Penn; John Donoghue; "Neuronal ensemble control of prosthetic devices by a human with tetraplegia"; 2006 Nature Publishing Group; vol. 442, Jul. 13, 2006; pp. 164-171.

Howard, Matthew; Bruce Abkes; Michael Ollendieck; Myounggya Noh; Rogers Ritter; George Gillies; Measurement of the Force Required to Move a Neurosurgical Probe Through in vivo Human Brain Tissue; IEEE Transactions on Biomedical Engineering, vol. 47, No. 7, Jul. 1999; pp. 891-894.

Howard, Matthew MD; M Sean Grady MD; Rogers Ritter PhD; George Gillies PhD; Elizabeth Quate BS; Jannelle Molloy MS; "Magnetic Movement of a Brain Thermoceptor"; Neurosurgery, vol. 24, No. 3, Mar. 1989, USA; pp. 444-448.

Ignatius, M J; N Sawhney; A Gupta; B M Thibadeau; O R Monteiro; I G Brown; "Bioactive surface coatings for nanoscale instruments: Effects on CNS neurons"; Conductive Biocompatible Materials; 1998 John Wiley & Sons, Inc.; pp. 264-274.

Kim, Dong-Hwan; David Martin; "Sustained release of dexamethasone from hydrophilic matrices using PLGA nanoparticles for neural drug delivery"; Biomaterials 27, 2006 Elsevier Ltd.; pp. 3031-3037.

Lagorce, Laure; Mark Allen; "Magnetic and Mechanical Properties of Micromachined Strontium Ferrite/Polyimide Composites"; IEEE Journal of Microelectromechanical Systems, vol. 6, No. 4, Dec. 1997; pp. 307-312.

Lee, Hyunjung; Ravi Bellamkonda; Wei Sun; Marc Levenston; "Biomechanical analysis of silicon microelectrode-induced strain in the brain"; Institute of Physics Publishing, J. Neural Eng 2 (Sep. 30, 2005); UK; pp. 81-89.

Lee, Kee-Keun; Jipling HE; Amarjit Singh; Stephen Massia; Gholamreza Ehteshami; Bruce Kim; Gregory Raupp; "Polyimide-based intracortical neural implant with improved structural stiffness"; 2004 Institute of Physics Publishing, J Micromech. Microeng. 14; Aug. 18, 2003; pp. 32-37.

McNEIL, Robert; Rogers Ritter; Bert Wang; Michael Lawson; George Gillies; Kevin Wika; Elizabeth Quate; Matthew Howard III; M Sean Grady; "Characteristics of an Improved Magnetic Implant Guidance System"; IEEE Transaction on Biomedical Engineering, vol. 42, No. 8, Aug. 1995; pp. 802-808.

McNEIL, Robert; Rogers Ritter; Bert Wang; Michael Lawson; George Gillies; Kevin Wika; Elizabeth Quate; Matthew Howard III; M Sean Grady; "Functional Design Features and Inital Performance Characteristics of a Magnetic-Implant Guidance System for Stereotactic Neurosurgery"; IEEE Transactions on Biomedical Engineering, vol. 42, No. 8, Aug. 1995; pp. 793-801.

Mercanzini, Andre; Karen Cheung; Derek Buhl; Marc Boers; Ann Maillard; Phillippe Colin; Jean-Charles Bensadoun; Arnaud Bertsch; Phillippe Renaud; "Demonstration of cortical recording using novel flexible polymer neural probes"; 2007 Elsevier, Sensors and Actuators A 143 (2008), pp. 90-96.

Metz, S; A Bertsch; D Bertrand; PH. Renaud; "Flexible polyimide probes with microelectrodes and embedded microfluidic channels for simultaneous drug delivery and multi-channel monitoring of bioelectric activity"; 2003 Elsevier, Biosensors & Bioelectronics 19 (2004); pp. 1309-1318.

Miller, John David; "Rowland's Magnetic Analogy to Ohm's Law"; The University of Chicago Press on behalf of the History of Science Society; vol. 66, No. 2; Jun. 1975; pp. 230-241.

Molloy, J A; R C Ritter; M S Grady; M A Howard III; E G Quate; G T Gillies; "Experimental Determination of the Force Required for Insertion of a Thermoseed Into Deep Brain Tissues"; Annals of Biomedical Engineering, vol. 18; 1990; pp. 299-313.

Moritz, Chet; Steve Perlmutter; Eberhard Fetz; "Direct control of paralysed muscles by cortical neurons"; 2008 Macmillan Publishers Limited; Nature; vol. 456, Dec. 4, 2008; pp. 639-643.

Nguyen, L T; A Lisfi; J C Lodder; "The effects of metallic underlayers on magnetic properties of obliquely sputtered Co thin films"; 2002 Elsevier Science, Journal of Magnetism and Magnetic Materials 242-245 (2002); pp. 374-377.

O'Brien, David; T Richard Nichols; Mark Allen; "Flexible Microelectrode Arrays with Integrated Insertion Devices"; 0-7803-5598-4/01 @2001 IEEE; pp. 216-219.

Oka, K; N Yano; S Furukawa; I Ogasawara; "Uniaxial Magnetic FeC Thin Films Sputtered onto Polymer Substrates"; IEEE Transactions on Magnetics, vol. 31, No. 6, Nov. 1995; pp. 3997-3999.

Otto, Steven, MA; Derald Brackmann, MD; Willam Hitselberger, MD: Robert Shannon, PhD; Johannes Kuchta, MD; "Multichannel auditory brainstem implant: update on performance in 61 patients"; J Neurosurg 96; Jun. 2002; pp. 1063-1071.

(56) References Cited

OTHER PUBLICATIONS

Petukhov, V Yu; N R Khabibullina, M I Ibragimova; A A Bukharaev; D A Biziaev; E P Zheglov; G G Gumarov; R Muller; "Magnetic Properties of Thin Metal-Polymer Films Prepared by High-Dose Ion-Beam Implantation of Iron and Cobalt Ions into Polyethylene Terephthalate"; Applied Magnetic Resonance (2007) 32; The Netherlands; Dec. 15, 2006; pp. 345-361.
Polikov, Vadim; Patrick Tresco; William Reichert; "Response of brain tissue to chronically implanted neural electrodes"; Elsevier, Journal of Neuroscience Methods 148 (2005); pp. 1-18.
Remove—Textbook: Ramo, "2.16 Gradient"; Fields and Waves, The Equations of Stationary Electric and Magnetic Fields; pp. 90-109.
Reich, Daniel; Ferenc Mechler; Keith Purpura; Jonathan Victor; Interspike Intervals, Receptive Fields, and Information Encoding in Primary Visual Cortex; 2000 Society for Neuroscience, The Journal of Neuroscience 20(5), Mar. 1, 2000; pp. 1964-1974.
Rennaker, R L; A M Ruyle; S E Street; A M Sloan; "An economical multi-channel cortical electrode array for extended periods of recording during behavior"; 2004 Elsevier, Journal of Neuroscience Methods 142 (2005); pp. 97-105.
Richardson-Burns, Sarah; Jeffrey Hendricks; David Martin; "Communication—Electrochemical polymerization of conducting polymers in living neural tissue"; 2007 IOP Publishing Ltd; Journal of Neural Engineering 4 (2007); UK; pp. L6-L13.
Richardson-Burns, Sarah; Jeffrey Hendricks; Brian Foster; Laura Povlich; Dong-Hwan Kim; David Martin; "Polymerization of the conducting polymer poly(3,4-ethylenedioxythiophene) (PEDOT) around living neural cells"; 2006 Elsevier Ltd., ScienceDirect, Biomaterials 28; 2007, pp. 1539-1552.
Rousche, Patrick; David Pellinen; David Pivin Jr.; Justin Williams; Rio Vetter; Daryl Kipke; "Flexible Polyimide-Based Intracortical Electrode Arrays with Bioactive Capability"; IEEE Transactions on Biomedical Engineering, vol. 48, No. 3, Mar. 2001; pp. 361-371.
Rutishauser, Ueli; Erin Schuman; Adam Mamelak; "Online detection and sorting of extracellularly recorded action potentials in human medical temporal lobe recordings, in vivo"; Journal of Neuroscience Methods, 2006; pp. 1-55.
Sanders, J E; C E Stiles; C L Hayes; "Tissue response to single-polymer fibers of varying diameters: Evaluation of fibrous encapsulation and macrophage density"; @ 2000 John Wiley & Sons, Inc. J Biomed Mater Res, 52; pp. 231-237.
Schmidt, E M; M J Bak; F T Hambrecht; C V Kufta; D K O'Rourke; P Vallabhanath; "Feasibility of a visual prosthesis for the blind based on intracortical microstimulation of the visual cortex"; Oxford University Press 1996; Brain (1996) 119; pp. 507-522.
Bresie, D A; J A Andrews, "Design of Reluctance Accelerator"; IEEE Transactions on Magnetics, vol. 27, No. 1, Jan. 1991; pp. 623-627.
Seymour, John; Daryl Kipke; "Neural probe design for reduced tissue encapsulation in CNS"; Elsevier, ScienceDirect, Biomaterials 28 (2007); pp. 3594-3607.
Shain, William, Leah Spataro; Jonathan Dilgen; Kraig Haverstick; Scott Retterer; Michael Isaacson; Mark Saltzman; James Turner; "Controlling Cellular Reactive Responses around Neural Prosthetic Devices using Peripheral and Local Intervention Strategies"; IEEE Transactions on Neural Systems and Rehabilitation Engineering, vol. 11, No. 2 Jun. 2003, pp. 186-188.
Sharp, Andrew; Hrishikesh Panchawagh; Alicia Ortega; Ryan Artale; Sarah Richardson-burns; Dudley Finch; Ken Gall; Roop Mahajan; Diego Restrepo; "Communication—Toward a self-deploying shape memory polymer neural electrode"; Institute of Physics Publishing, Journal of Neural Engineering 3 (2006); pp. L23-L30.
Singh, Amarjit; Gholamreza Ehteshami; Stephen Massia; Jiping He; Robin Storer; Gregory Raupp; "Glial cell and fibroblast cytotoxicity study on plasma-deposited diamond-like carbon coatings"; Elsevier Biomaterials 24 (2003); pp. 5083-5089.
Softky, William; Christof Koch; "The Highly Irregular Firing of Cortical Cells is Inconsistent with Temporal Integration of Random EPSPs"; The Journal of Neuroscience, Janaury 1993 13(1); pp. 334-350.
Stieglitz, Thomas; Matthias Gross; "Flexible BIOMEMS with electrode arrangements on front and back side as key component in neural prostheses and biohybrid systems"; Elsevier Sensors and Actuators B 83 (2002); pp. 8-14.
Strumwasser, Felix; "Long-Term Recording from Single Neurons in Brain of Unrestrained Mammals"; Science, New Series, vol. 127, No. 3296 (Feb. 28, 1958), pp. 469-470.
Subbaroyan, Jeyakumar; David Martin; Daryl Kipke; "A finite-element model of the mechanical effects of implantable microelectrodes in the cerebral cortex"; Institute of Physics Publishing, Journal of Neural Engineering 2, (2005); UK; pp. 103-113.
Swindle, M Michael; George Volger; Linda Fulton; Robert Marini; Sulli Popilskis; "Preanesthesia, Anesthesia, Analgesia, and Euthanasia", Chapter 22; Laboratory Animal Medicine, 2nd Edition; Elsevier Science; USA; pp. 955-1003.
Szarowski, D H; M D Andersen; S Retterer; A J Spence; M Isaacson; H G Craighead; J N Turner; W Shain; "Brain responses to micromachines silicon devices"; Elsevier, Science Direct, Brain Research 983 (2003); pp. 23-35.
Takeuchi, Shoji; Takafumi Suzuki; Kunihlko Mabuchi; Hiroyuki Fujita; "3D flexible multichannel neural probe array"; Institute of Physics Publishing, Journal of Micromechanics and Microengineering 14 (2004); pp. 104-107.
Takeuchi, Shoji; D Ziegler; Y Yoshida; K Mabuchi; T Suzuki; "Parylene flexible neural probes integrated with microfludic channels"; The Royal Society of Chemistry 2005, Lab Chip, 2005, 5; pp. 519-523.
Wang, Welsong; Zhongmel Yao; Jackie Chen; Ji Fang; "Composite elastic magnet films with hard magnetic feature"; Institute of Physics Publishings, Journal of Micromechanics and Microengineering 14 (2004); pp. 1321-1327.
Weppelmann, E R; J S Field; M V Swain; "Observation, analysis, and simulation of the hysteresis of silicon using ultra-micro-indentation with spherical indenters"; 1993 Materials Research Society, J Mater Res, vol. 8, No. 4, Apr. 1993; pp. 830-840.
Williams, Justin; Joseph Hippensteel; John Dilgen; William Shain; "Complex impedance spectroscopy for monitoring tissue responses to be inserted neural implants"; IOP Publishing, Journal of Neural Engineering 4 (2007); pp. 410-423.
Williams, Justin; Robert Rennaker; Daryl Kipke; "Long-term neural recording characteristics of wire microelectrode arrays implanted in cerebral cortex"; 1999 Elsevier Brain Research Protocols 4 (1999); pp. 303-313.
Winter, Jessica; Stuart Cogan; Joseph Rizzo III; "Neurotrophin-Eluting Hydrogel Coatings for Neural stimulating Electrodes"; 2006 Wiley Periodicals, Inc., Wiley InterScience; J Biomed Mater Res Part B: Appl Biomater 81B; Oct. 13, 2006; pp. 551-563.
Zhong, Yinghui; Ravi Bellamkonda; "Controlled release of anti-inflammatory agent a-MSH from neural implants"; 2005 Elsevier, Science Direct, Journal of Controlled Release 106 (2005); pp. 309-318.
Ziegler, Dominik; Takafumi Suzuki; Shoji Takeuchi; "Fabrication of Flexible Neural Probles With Built-In Microfluidic Channels by Thermal Bonding of Parylene"; 2006 IEEE Journal of Microelectromechanical Systems, vol. 15, No. 6, Dec. 2006; pp. 1477-1482.

* cited by examiner

FLEXIBLE NEURAL PROBE FOR MAGNETIC INSERTION

RELATED APPLICATIONS

This application is a continuation of International Patent Application PCT/US09/66075 filed Nov. 30, 2009, which claims priority to U.S. Patent Application Ser. No. 61/118,628 filed Nov. 30, 2008, both of which are incorporated by reference herein.

GOVERNMENT RIGHTS

This invention was made with government support under Grant Number NA/IND010674 awarded by USDA/NIFA. The Government has certain rights in the invention.

TECHNICAL FIELD OF THE DISCLOSURE

The present invention relates generally to implantable electrodes, and more particularly, to flexible electrodes used with neural tissues.

BACKGROUND OF THE DISCLOSURE

Since their first use fifty years ago, chronic implantable electrodes have become a critical tool for exploring the function of neural tissue. In fact, chronic electrode recordings have contributed to the basic understanding of how neural networks process sensory stimuli and impart motor control. Moreover, these same electrodes can be used to actively stimulate regions of the brain, as well as to mimic natural sensory input and to initiate physical responses.

The ability to interface directly with the brain is making it possible for the blind to see, the deaf to hear, and the paralyzed to move. However, while great strides have been made in neural interfacial technologies, signal degradation due glial scar formation still limits the functional lifespan of chronically implanted electrodes.

The continued presence of an implanted electrode initiates a chronic foreign body reaction. Over time, the body isolates to the probe; activated astrocytes and microglia encapsulate the electrode, effectively displacing local neurons, hindering diffusion, and increasing interfacial impedance. Micromotion of the probe relative to surrounding tissue exacerbates this phenomenon, enhancing scar tissue formation in high stress areas.

One of the fundamental problems with current electrodes is the dichotomy between the material properties needed for implantation and the properties required to minimize long term neural trauma. Current microelectrodes must be stiff enough to retain their shape under the compressive load needed to drive them through neural tissue. Silicon microelectrodes possess the required stiffness but sacrifice flexibility. Moreover, the large mismatch between the modulus of silicon based probes (~172 GPa) and the brain (~0.1 MPa) has been identified as a contributing factor in glial scar formation and subsequent long term signal degradation. Efforts have been made to reduce scarring by developing coatings which improve neural cell attachment and growth and prevent astrocyte adhesion. However, such measures fail to address the severe mechanical mismatch between neural tissue and the probes themselves.

A number of relatively flexible probes have been developed to reduce micromotion-induced tissue strain. Such devices are typically fabricated from polymers such as polyimide using Bio-MEMS techniques, and have elastic moduli of ~2 GPa. Implantation using traditional techniques is difficult due to their increased flexibility. Previous approaches have attempted to address this issue by creating an incision in the pia prior to insertion and/or creating a shape memory probe that slowly exerts force on neural tissue, allowing for gradual plastic deformation of the tissues surrounding the device. Still other approaches have developed techniques for polymerizing flexible conductive poly(3,4-ethylenedioxythiophene) in direct contact with living neural tissue, stiffened polymeric probes by means of fluid filled channels, bonded stiff metallic elements to the polymer and/or used ridged structures to penetrate the tissue, leaving the flexible probe behind after withdrawal. Despite using soft materials, the majority of such devices must compromise flexibly for the ability to exert enough compressive force for implantation.

SUMMARY OF THE INVENTION

The present invention overcomes or ameliorates at least one of the prior art disadvantages discussed above or provides a useful alternative thereto by providing a novel system for implanting a flexible neural probe by using an induced magnetic field to accelerate a magnetic tip tethered to a flexible length of conductive wire into neural tissue. In accordance with certain aspects of the present invention, the tether is pulled by the magnetic tip and held in tension during insertion to prevent buckling. Preliminary in vivo results have demonstrated that even though the current dimensions of the recording tip have somewhat limited spatial resolution, these inventive probes can be used to discriminate single unit activity. As such, it is envisioned that further refinement of the inventive embodiments will make it possible to safely implant soft, flexible probes in an accurate and precise manner into deep brain structures for chronic neural recording. Moreover, the concurrent use of flexible electrode materials is envisioned to reduce micromotion-induced stress, thereby lessening the severity of chronic glial scarring.

In one form thereof a neural probe deployment system is disclosed. The system comprises a magnetic probe, a magnetic field generator acting on the magnetic probe, a first guiding tube disposed on a first side of the magnetic field generator, wherein the magnetic probe is loaded inside the first guiding tube, and a second guiding tube disposed on a second side of the magnetic field generator, wherein activation of the magnetic field generator propels the magnetic probe from the first guiding tube through the second guiding tube, thereby deploying the magnetic probe.

In another form thereof, a deployment system for probing a tissue is provided. In accordance with this embodiment, the system comprises a magnetic probe tethered to a moveable platform and positioned on a first side of the tissue, and a stationary magnetic field generator acting on the magnetic probe and positioned on a second side of the tissue, the stationary magnetic field generator being configured to place tension on the magnetic probe tether during activation, thereby causing the magnetic probe to contact the tissue.

BRIEF DESCRIPTION OF THE DRAWINGS

The above-mentioned and other advantages of the present invention, and the manner of obtaining them, will become more apparent and the invention itself will be better understood by reference to the following description of the embodiments of the invention taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
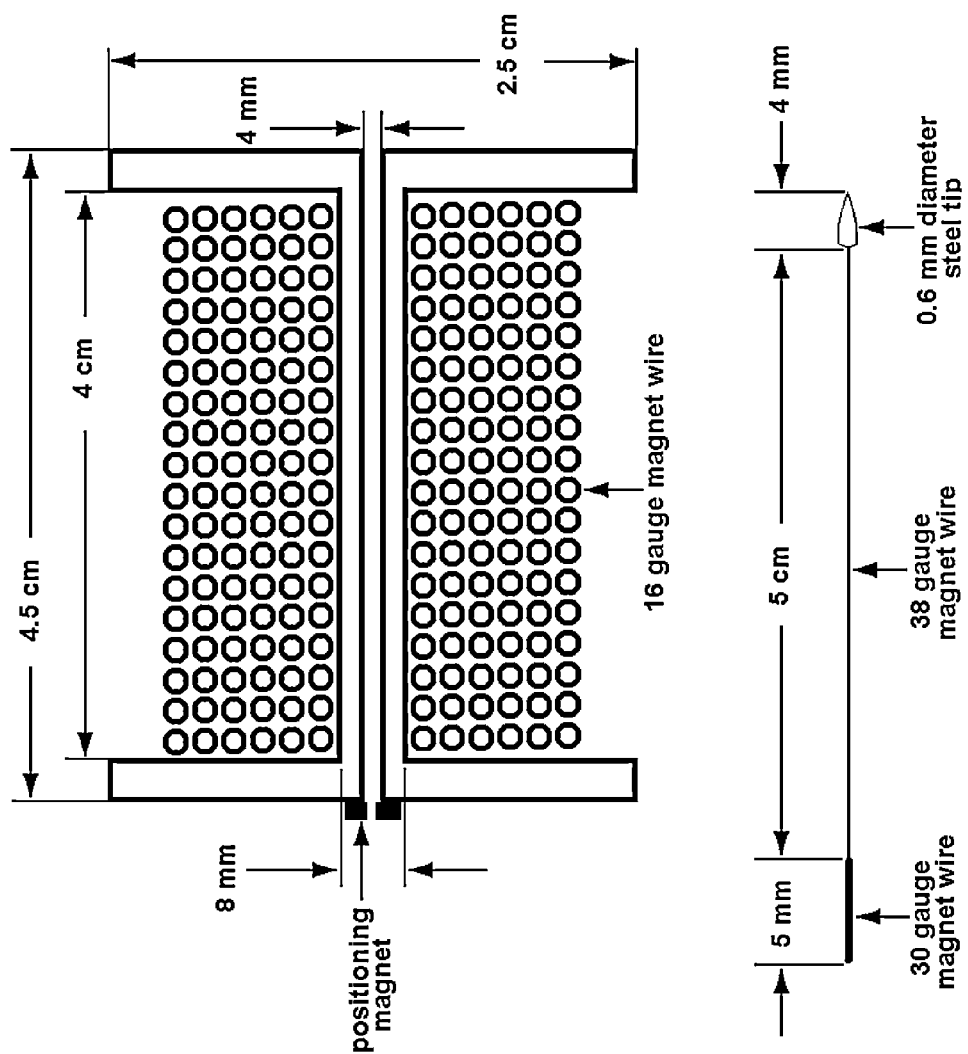
FIG. 1 is a cross-sectional schematic of an inductive coil and electrode in accordance with the present invention.
Figure 2A:
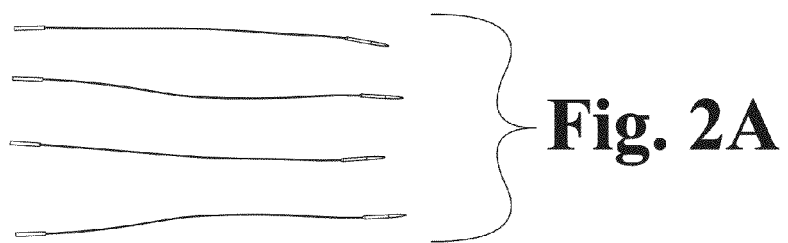
FIG. 2A is an image of electrodes for use in accordance with the teachings of the present invention.
Figure 2B:
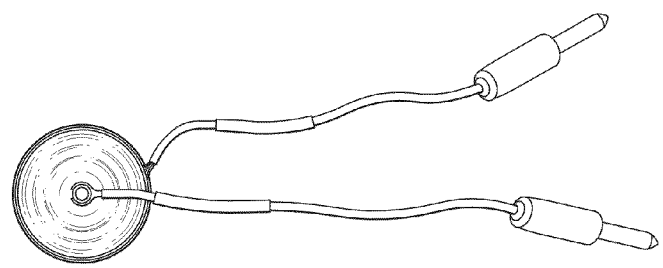
FIG. 2B is an image of an inductive coil with a magnet for use in accordance with the teachings of the present invention.
Figure 2C:
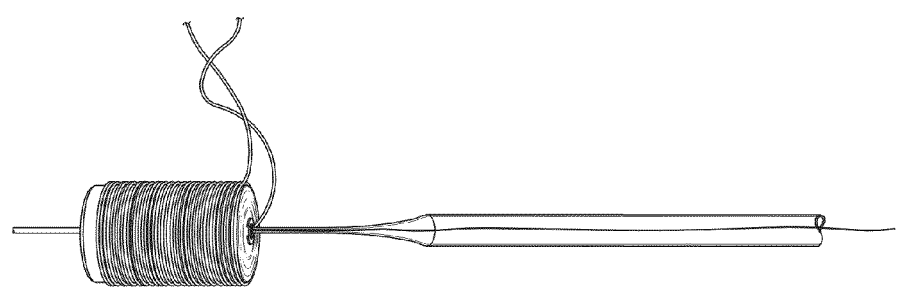
FIG. 2C is an image of glass pipette loaded with an electrode for use in accordance with the teachings of the present invention.
Figure 2D:
FIG. 2D is an image of the assembled implantation device with a positioned electrode for use in accordance with the teachings of the present invention.

Referring to FIG. 1, a cross-sectional schematic of a prototype inductive coil and electrode constructed in accordance with certain aspects of the present invention is shown. Specifically, an inductive coil was constructed by wrapping 6 rows of 16 gauge copper heavy armored poly-thermaleze magnet wire (Belden) around a polyethylene spindle. The coil was measured to have an inductance of 110 µH and resistance of 118 mΩ. A small toroidal magnet was placed at one end of the coil to position the electrode prior to insertion, and a 9" borosilicate glass Pasteur pipette (VWR) was inserted into the coil to act as the ejection tube (see FIG. 2, which shows (A) an image of illustrative electrodes useful in accordance with the present invention; (B) the top view of an exemplary inductive coil with a magnet (arrow) useful in accordance with the present invention; (C) a glass pipette loaded with an electrode in accordance with the present invention; and (D) an assembled implantation device with a positioned electrode (arrow) in accordance with the teachings of the present invention (scale bar represents 1 cm)).

With respect to the electrode design, a smooth conical steel tip (maximum diameter 0.6 mm; length 4 mm; mass 7.2±0.4 mg (n=7)) was soldered to a 5 cm length of 38-gauge copper heavy armored poly-thermaleze magnet wire (Belden). A section of stripped 30-gauge copper magnet wire was attached to the opposite end of the lead to serve as a recording interface (see FIG. 1). The assembled insertion system is depicted in FIG. 2. The total mass of the probe (steel tip and wire) was measured to be 14.8±0.6 mg. To decrease the recording surface area, the steel probe tip was dip coated in a polystyrene solution. Following the coating procedure, the end of coated probe tip was scraped with a scalpel blade to expose the recording surface.

Figure 3:
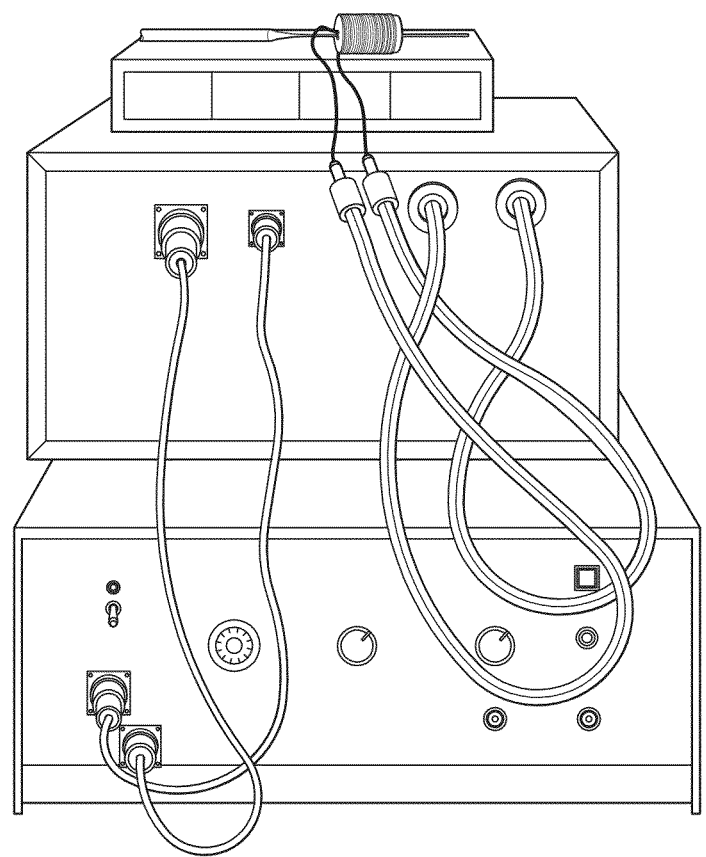
FIG. 3 is an image of a variable capacitor bank for use in accordance with the teachings of the present invention.

To characterize the implantation depth in accordance with certain aspects of the present invention, a capacitive system (which provided a pulsed electrical current) was utilized. The system consisted of a 900 µF capacitor bank which could be variably charged from about 0 to about 800 Volts (see FIG. 3). The capacitor bank discharged through the inductive coil into a separate uncharged 900 µF capacitor bank, and the magnetic field generated by this discharge accelerated the electrode through the coil, thereby imparting kinetic energy.

Electrode penetration depth relative to charge voltage was modeled using a 0.5 wt % agar gel brain model that was previously used by Das et al. (2007) to assess neural interface micromechanics (see Das et al., 2007). A 6 ml volume of hot 0.5% agar solution was introduced to 12 mm×75 mm glass culture tubes (VWR) and then allowed to set overnight at room temperature prior to testing. The pipette tip was aligned with the agar vial 2 mm above the surface of the gel and the penetration depth relative to charge voltage was characterized by measuring the distance between the probe tip and the agar surface after insertion. Moreover, the voltage was varied from 80 to 800 V at 80 volt increments with n=5 replications per insertion condition.

Figure 4:
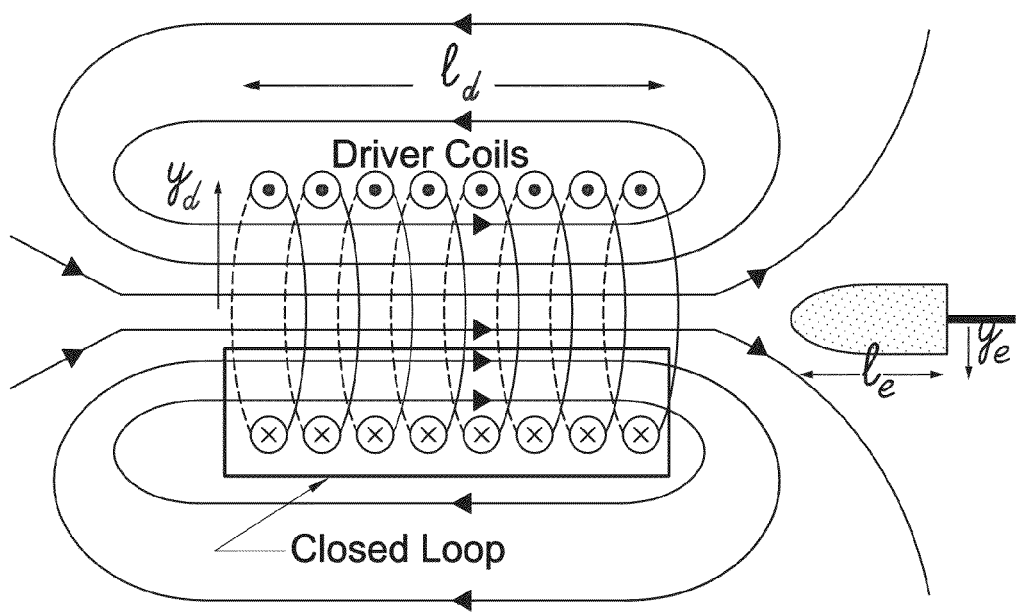
FIG. 4 is a drawing showing magnetic field lines through a driver coil and closed loop as used in accordance with Ampere's circuital law.

To achieve a first order approximation for the functionality of the magnetic electrode driver, a mathematical model is derived from electromagnetic theory. The magnetic field generated by the driver coil is first found using Ampere's circuital law in line integral form around a closed loop (Cheng, 1989). Referring to FIG. 4, which shows a drawing of magnetic field lines through the driver coil and the closed loop used in Ampere's circuit law, the loop intersects N turns of the driver and thus the injected current is multiplied by that factor. The magnetic field is perpendicular to the left and right sides of the closed loop and thus there is no contribution at those sides. The bottom side is outside of the driver where the magnetic field is approximated to be negligible. Assuming that the permeability of the relatively small electrode does not significantly change the magnetic field generated by the driver, the following equation is derived $$B \approx \frac{\mu_0 I_d N}{l_d}, \qquad (1)$$

where B is the magnetic field (or magnetic flux density), $\mu_0$ is the permeability in free space, $I_d$ is the current injected, N is the number of turns, and $l_d$ is the length of the driver.

The magnetic flux is determined using $$\Phi_B = BA = \frac{\mu_0 I_d N}{l_d} \pi r_d^2, \qquad (2)$$

where $\Phi_B$ is the magnetic flux, $r_d$ is the radius of the driver, and A is the cross-sectional area that is penetrated by the magnetic field.

The following analysis of this magnetic system is analogous to electric circuits where the magnetic flux law is similar to Ohm's law and magnetic flux, magnetomotive force, and reluctance are related to current, voltage, and resistance, respectively. When the electrode is in the driver coil, only a portion of the magnetic flux generated by the driver is absorbed by the electrode. This tendency of the material to absorb magnetic flux is defined as reluctance. The portion of the total flux through the driver cross-section which passes through the electrode is determined by the ratio of reluctances as:

$$\Phi_e = \Phi_B \frac{\mathcal{R}_{d-e}}{\mathcal{R}_{d-e} + \mathcal{R}_e} \tag{3}$$

where $\Phi_e$ is the magnetic reluctance penetrating the electrode, $R_{d-e}$ is the reluctance of the driver free-space volume around the electrode, and $R_{d-e}$, and $R_e$ is the reluctance of the electrode. The reluctances, as derived in (Sears, 1954), are given by $$\mathcal{R}_{d-e} = \frac{l_e}{\mu_0(\pi r_d^2 - \pi r_e^2)}, \mathcal{R}_e = \frac{l_e}{\mu_e \pi r_e^2}, \tag{4}$$

where $r_e$ is the radius of the electrode, $l_e$ is the length of the electrode, and $\mu_e$ is the permeability of the electrode. It should be noted that the length of the electrode within the driver coil varies during entry, but due to the short duration of entry, the length is assumed to be constant. Similar to resistance, reluctance is proportional to length and inversely proportional to cross-sectional area. As the permeability of the electrode increases the reluctance decreases causing more flux to flow through the electrode in the parallel network. This inverse relationship between reluctance and permeability is analogous to resistance and conductivity in electric circuits. The magnetic energy induced in the electrode is equal to the work done and, as described in (Bresie and Andrews, 1991), is related to magnetic flux and reluctance through $$E_m = \frac{1}{2}\Phi_e^2 \mathcal{R}_e. \tag{5}$$

Force is defined as work divided by distance and thus the force on the electrode is equal to the magnetic energy absorbed by the electrode over the length of the driver coil. A linear approximation is used for the total amount of work done over the duration when the electrode is still in the driver coil. Using equations (1)-(5) the force is given by:

$$F = \frac{l_e \mu_0 I_d^2 N^2 \pi r_d^4}{2 r_e^2 l_d^2} \left( \frac{\mu_e r_e^2}{\mu_e r_e^2 + \mu_0(r_d^2 - r_e^2)} \right)^2. \tag{6}$$

With a zero initial velocity, the velocity after a specific time period is determined by the accumulated acceleration over that amount of time. This velocity is found by integrating the acceleration over the period as $$v_e = \left( \frac{\mu_e r_e^2}{\mu_e r_e^2 + \mu_0(r_d^2 - r_e^2)} \right)^2 \frac{l_e \mu_0 N^2 \pi r_d^4}{2 m_e r_d^2 l_d^2} \int_0^{t_1} I_d^2(t) dt, \tag{7}$$

where the current $I_d(t)$ is a function of time and $m_e$ is the mass of the electrode.

The mechanics of the magnetic driver begin with charging up a capacitor bank to an initial voltage. A switch is then opened, feeding the charge from the capacitor bank through the driver coil. The transient current does not instantly reach the initial voltage over the resistance of the driver because the inductance opposes the change in current. Thus current that the inductor allows to flow is related to time by:

$$I_d(t) = \frac{V}{R_d}(1 - e^{-t/(L_d/R_d)}), \tag{8}$$

where V is the voltage on the capacitor, $R_d$ is the series resistance and $L_d$ is the inductance of the driver coil. The situation is a little more complex because the voltage on the capacitor is a function of time as it decreases due to the draining of charge. This transient voltage is given by:

$$V(t) = V_i - \frac{I_d(t)}{C} t \tag{9}$$

where C is the capacitance of the capacitor bank. Using (9) in (8) and solving for $I_d(t)$ gives the following relationship $$I_d(t) = \frac{V_i C(1 - e^{-t/(L_d/R_d)})}{R_d C + t(1 - e^{-t/(L_d/R_d)})}. \tag{10}$$

Incorporating the transient current into the force and velocity equations gives the final equations:

$$F = K \frac{l_e \mu_0 N^2 \pi r_d^4}{2 r_e^2 l_d^2} \times \left( \frac{\mu_e r_e^2}{\mu_e r_e^2 + \mu_0(r_d^2 - r_e^2)} \frac{V_i C(1 - e^{-t/(L_d/R_d)})}{R_d C + t(1 - e^{-t/(L_d/R_d)})} \right)^2, \tag{11}$$

$$v_e = K \left( \frac{\mu_e r_e^2}{\mu_e r_e^2 + \mu_0(r_d^2 - r_e^2)} \right)^2 \tag{12}$$

$$\frac{l_e \mu_0 N^2 \pi r_d^4}{2 m_e r_e^2 l_d^2} \times \int_0^{t_1} \left( \frac{V_i C(1 - e^{-t/(L/R)})}{RC + t(1 - e^{-t/(L/R)})} \right)^2 dt.$$

where K is a calibration constant which accounts for the simplifications and assumptions used in the derivations. The position in free space is determined by integrating the velocity over time as:

$$x_e = K \left( \frac{\mu_e r_e^2}{\mu_e r_e^2 + \mu_0(r_d^2 - r_e^2)} \right)^2 \tag{13}$$

$$\frac{l_e \mu_0 N^2 \pi r_d^4}{2 m_e r_e^2 l_d^2} \int_0^{t_1} \int \left( \frac{V_i C(1 - e^{-t/(L/R)})}{RC + t(1 - e^{-t/(L/R)})} \right)^2 dt dt.$$

This position equation is needed to determine when the electrode has exited the driver and no longer sees a force. This is based on the assumption that outside of the driver coil, the magnetic field is negligible.

The velocity determines the kinetic energy of the electrode. This energy along with the estimated force required to penetrate the brain is used to determine the penetration depth. The penetration depth as a function of electrode velocity is given by $$d_p = \frac{m_e v_e^2}{2F_b} \quad (14)$$

where $d_p$ is the penetration depth and $F_b$ is the force required to penetrate through the brain. These equations are incorporated in a Matlab script to determine the forces and velocities of the electrode as a function of initial voltages and electrode size.

Figure 5:
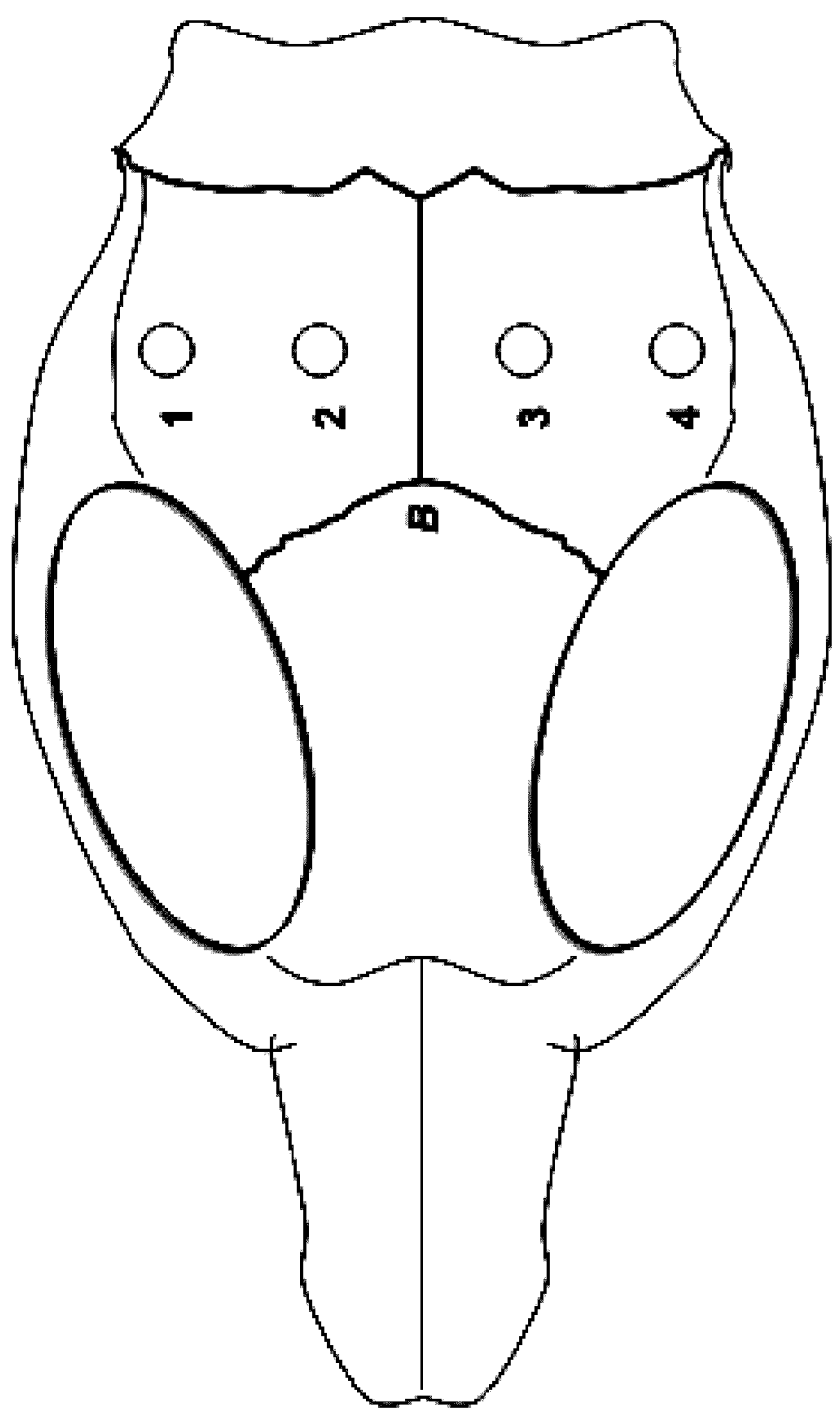
FIG. 5 depicts various electrode implant locations in accordance with the present invention.
Figure 6B:
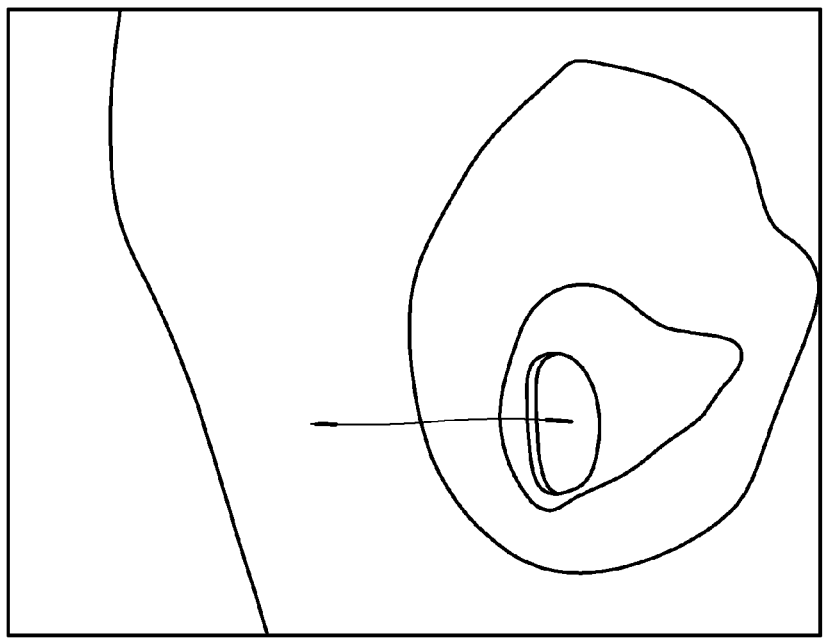
FIG. 6B is an image of implantation system immediately after electrode insertion in accordance with the teachings of the present invention.
Figure 6A:
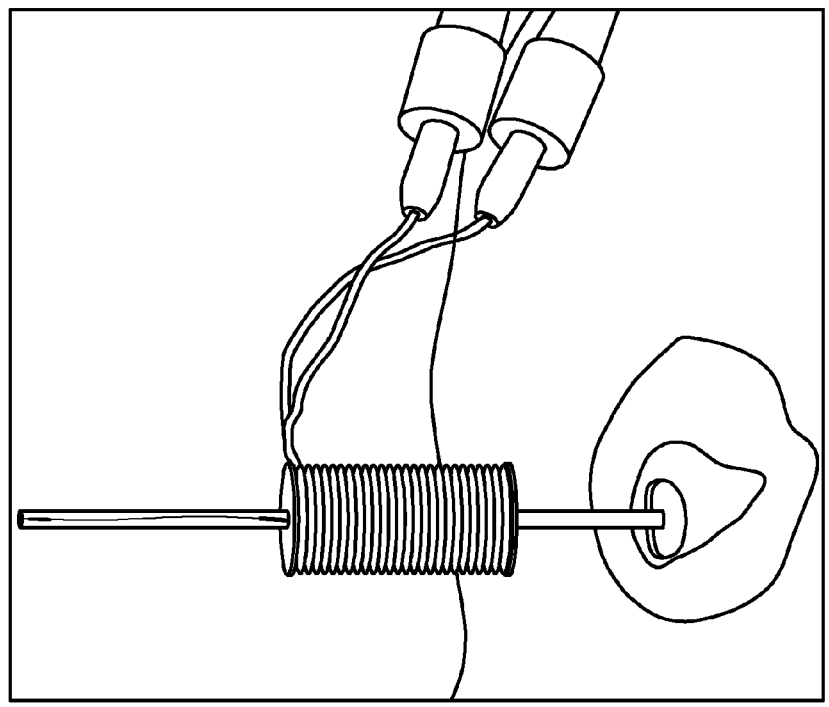
FIG. 6A is an image of an implantation system prior to electrode insertion in accordance with the teachings of the present invention.

An exemplary embodiment describing an electrode implantation process in accordance with the present invention is now provided. The surgical and animal handling procedures in accordance with this exemplary embodiment were approved by the Purdue Animal Care and Use Committee (PACUC) prior to performing the study and adhered to the NIH guidelines for the care and use of laboratory animals. The first subject was a 320 g female Long Evans rat. Anesthesia was induced via 5% Isoflurane in 2 L/min $O_2$ and maintained using 0.5 to 3% Isoflurane in 2 L/min $O_2$ (Swindle, 2002). Post induction, the surgical site was shaved and cleaned with alternating scrubs of Dial Surgical Scrub and Betadine. Using a standard stereotactic frame (David Kopf Instruments, Tujunga, Calif., USA), a midline incision was made and the skull was cleaned to expose lambda, bregma, and the four proposed craniotomy sites (right and left S1BF and S1HL) (see FIG. 5, which shows electrode implant locations for four (4) electrodes. Each electrode was inserted through a drill hole ~1 mm in diameter using the insertion device. Electrode 1 and 4 were inserted 4 mm posterior and 5 mm lateral to bregma (B) on opposing sides of midline. The desired implant location for these electrodes were the right and left S1BF (barrel field cortex) (Paxinos and Watson, 2007). Electrodes 2 and 3 were inserted 4 mm posterior and 2 mm lateral to bregma on opposing sides of midline. The desired implant location for these electrodes where the right and left S1HL (hindlimb region) (Paxinos and Watson, 2007). Electrode 3 was tied to ground and used as a reference during data collection). All drill locations were marked prior to drilling with a sterile ruler and cauterizer (Bovie Medical Corporation, St. Petersburg, Fla., USA). Four single holes drilled with a trephine bit served as craniotomies through which the probes were inserted. The dura was not removed prior to insertion. The inductive coil was affixed to a micromanipulator and the insertion channel tip was aligned 2 mm above the craniotomy site (FIG. 6A). A probe was loaded into the insertion channel and positioned by the magnet located above the coil. Based on the depth calibration data gathered using agar gel, the capacitor bank was charged to 320 V in order to achieve 4 mm of penetration. The presence of meningeal tissue prevented insertion under these conditions. Voltage was subsequently increased to 480 (craniotomy 1, FIG. 5) and 560 V (craniotomies 2-4) to achieve a penetration depth of ~3 mm and ~4 mm respectively (FIG. 6B). After inserting all four electrodes, the remaining exposed dura mater was covered using Kwik-Sil silicone elastomer (World Precision Instruments, Inc., Sarasota, Fla., USA). Dental cement was then used to cover the remaining skull surface to help hold the electrodes in place during data collection.

Six replicates of the polystyrene-coated probes were evaluated in 1× phosphate-buffered saline (1×PBS; pH=7.4) through electrochemical impedance spectroscopy (EIS) (Barsoukov and Macdonald, 2005). Impedances, measured using a two-electrode setup on a custom-built board and accompanying software, were obtained from 1 to 10 kHz using fixed 100 $mV_{pp}$ sinusoidal waveforms. A copper wire was used as a return path for the input sinusoid where reactance and resistance data were extracted from the observed current (Williams et al., 2007). All impedance data sets were analyzed in Matlab R2007a.

All neural recordings were obtained using a custom-built multiplexing headstage and accompanying software. Each recording amplifier on the headstage has a 150 Hz high-pass filter at its input, prohibiting conventional local field potential recording. Spike data was sorted using a modified version of Ueli Rutishauser's freely available spike-sorting package OSort (Rutishauser et al., 2006). In brief, the software first band-pass filters the raw signal from 0.3 to 3 kHz. A running average of the power in the signal is then calculated. If the local power of the filtered signal is at any point greater than 3× the standard deviation of the average signal power, a 2.5 ms window is extracted from the filtered signal, upsampled to 100 kHz, and sorted. Additional details are found in (Rutishauser et al., 2006).

Figure 7:
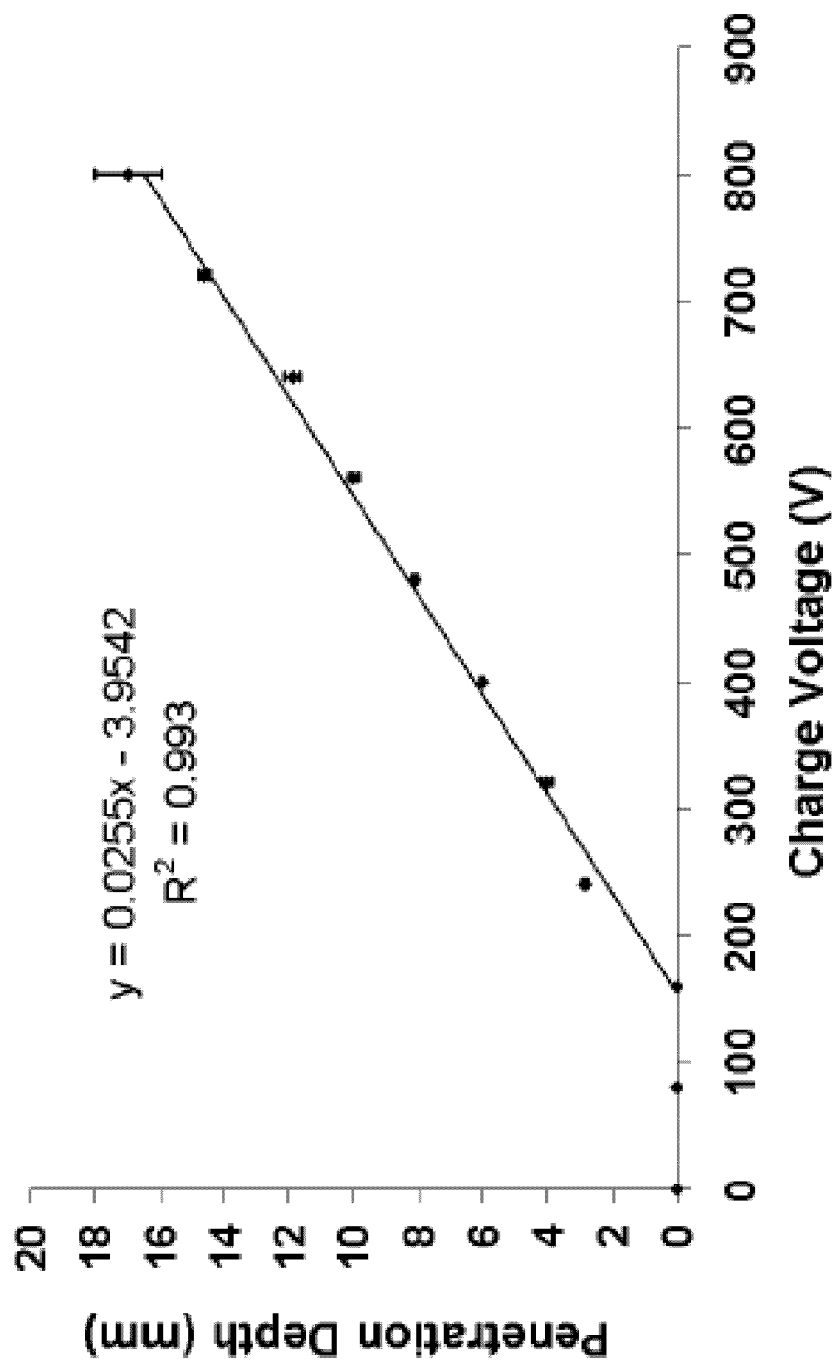
FIG. 7 is a graph showing probe penetration depth modeled using 0.5% agar gel relative to capacitor charge voltage.

A linear relationship between the charge voltage and penetration depth was observed ($R^2$=0.993) using a homogeneous 0.5% agar gel (FIG. 7). The average standard deviation in implantation depth was determined to be ±0.3 mm with condition specific deviation ranging between a minimum of ±0.1 mm (240 V) and maximum of ±1.0 mm (800 V). A charge of 80 V and 106 V did not overcome the positioning magnet's attractive force and the probe was not ejected.

Simulations were run using the appropriate values for dimensions, capacitances, voltages, masses, and other parameters in accordance with the inventive system as described above. With an initial voltage of 400 V, the current spike after closing the switch had a maximum amplitude of about 520 A, which produced a maximum force of about 10 N on the electrode. This force drives the electrode up to a velocity of 126.25 m/s.

Figure 8:
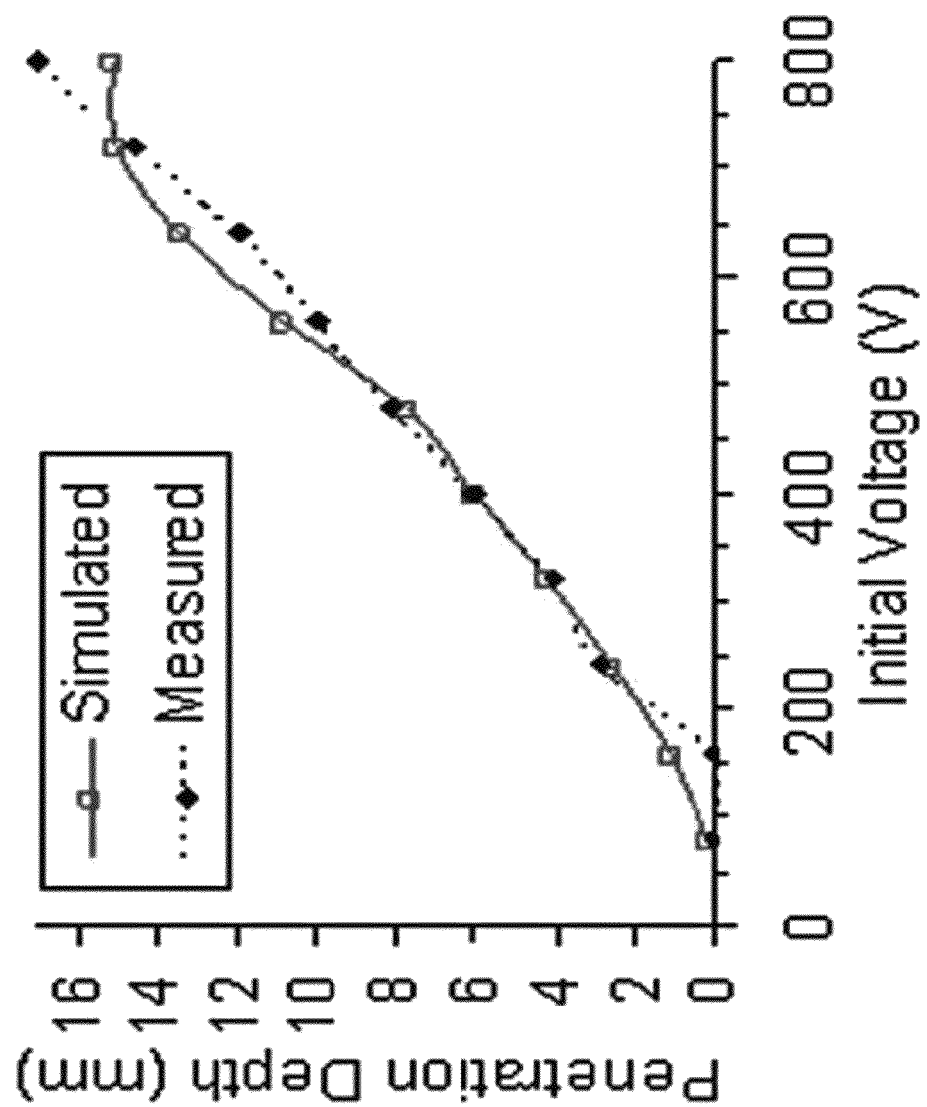
FIG. 8 is a graph showing the comparison of simulated and measured penetration depths in accordance with the teachings of the present invention.

The simulated results using the calibration constant, derived from a comparison between the simulated versus measured penetration depths (k=0.356), are plotted alongside the measured values in FIG. 8. This plot shows that the variation of simulated penetration depths as a function of initial voltage is comparable with the measured results.

Figure 9:
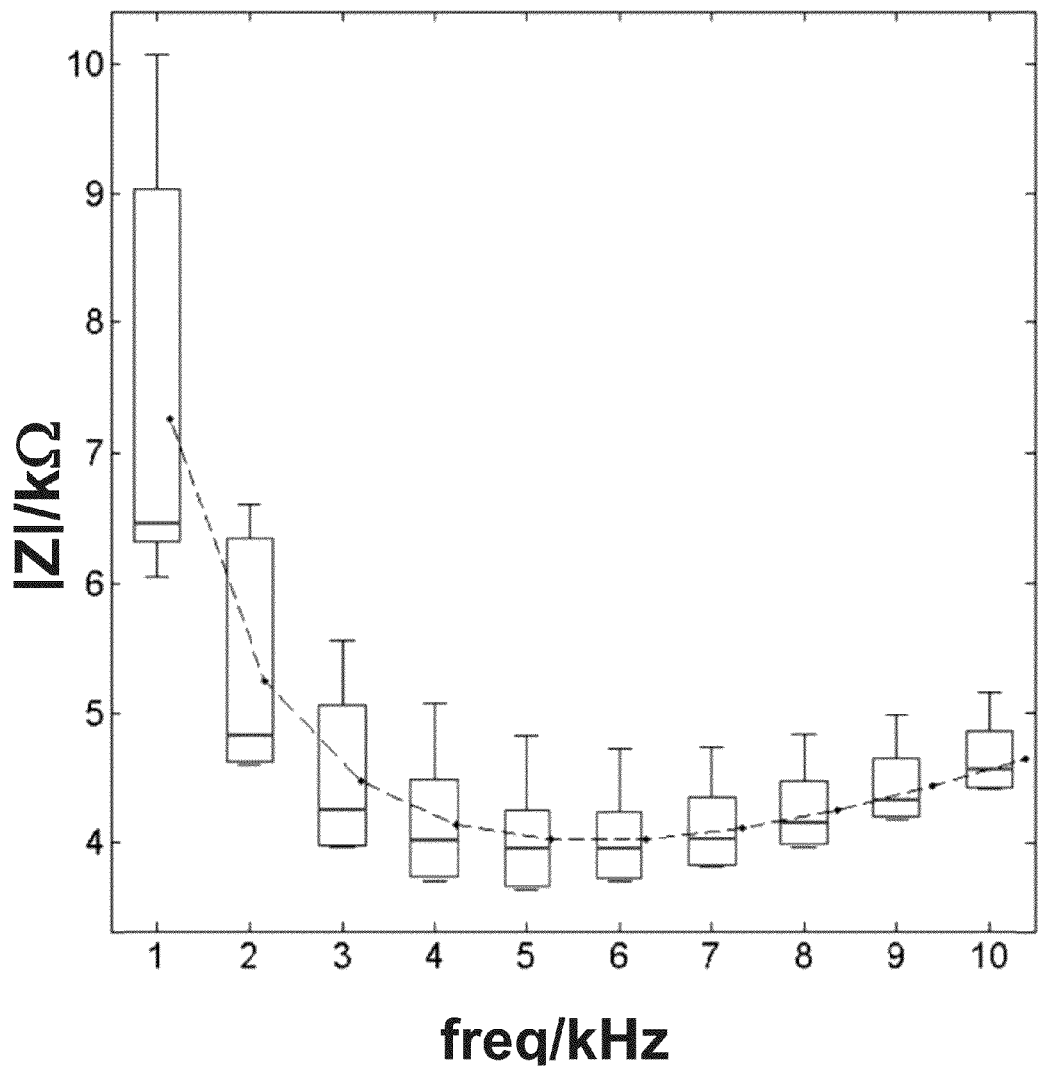
FIG. 9 is a graph showing average impedances and accompanying distributions.

FIG. 9 presents the mean impedances and the associated impedance distributions from the 6 coated probes evaluated in 1×PBS (pH 7.4 over a frequency range of 1-10 kHz. The solid line within each box-and-whisker plot indicates the median impedance over the sweep range. The dotted black line shows the mean impedance corresponding to the data presented in the box-and-whisker plots. The separation between the mean and median impedance at lower frequencies shows a slight skew in the data due to contributions from some relatively high impedance electrodes and an increasing variability in measurements at lower frequencies. Impedances at 1 kHz ranged from 6 to 10 kHz, with a mean impedance of 7.26±0.76 kHz (reported as mean±s.e.). The low mean impedance indicates that on average, the electrodes have relatively large recording surface areas. This means that the current probe design is not ideal for single-unit recording (Cogan, 2008). However, as indicated by the separation distance between the mean and median impedances at lower frequencies, some probes tended to have higher impedances. These probes have a higher probability of recording single-units due to a decreased recording site area and an accompanying improved spatial resolution.

Electrodes were successfully inserted through ~3.14 $mm^2$ craniotomies with the meninges intact. In cases where probe tips did not fully insert into their target regions, the probes slowly slid out of the insertion site. This indicates that the current probe design may exert excessive pressure on surrounding neurons. This sudden increase in pressure slowly pushes out the conical electrode when the conical probe tip is not fully inserted.

Neural activity from the probes that reached their target depths was successfully recorded, including some single-unit data on electrode 4. A segment of the bandpass-filtered (pass band: 0.3 to 3 kHz) neural signal from electrode 4 is presented in FIG. 10A along with sorted single-unit data (FIG. 10B) and accompanying interspike interval (ISI) histograms (FIGS. 10C, D).

Figure 10A:
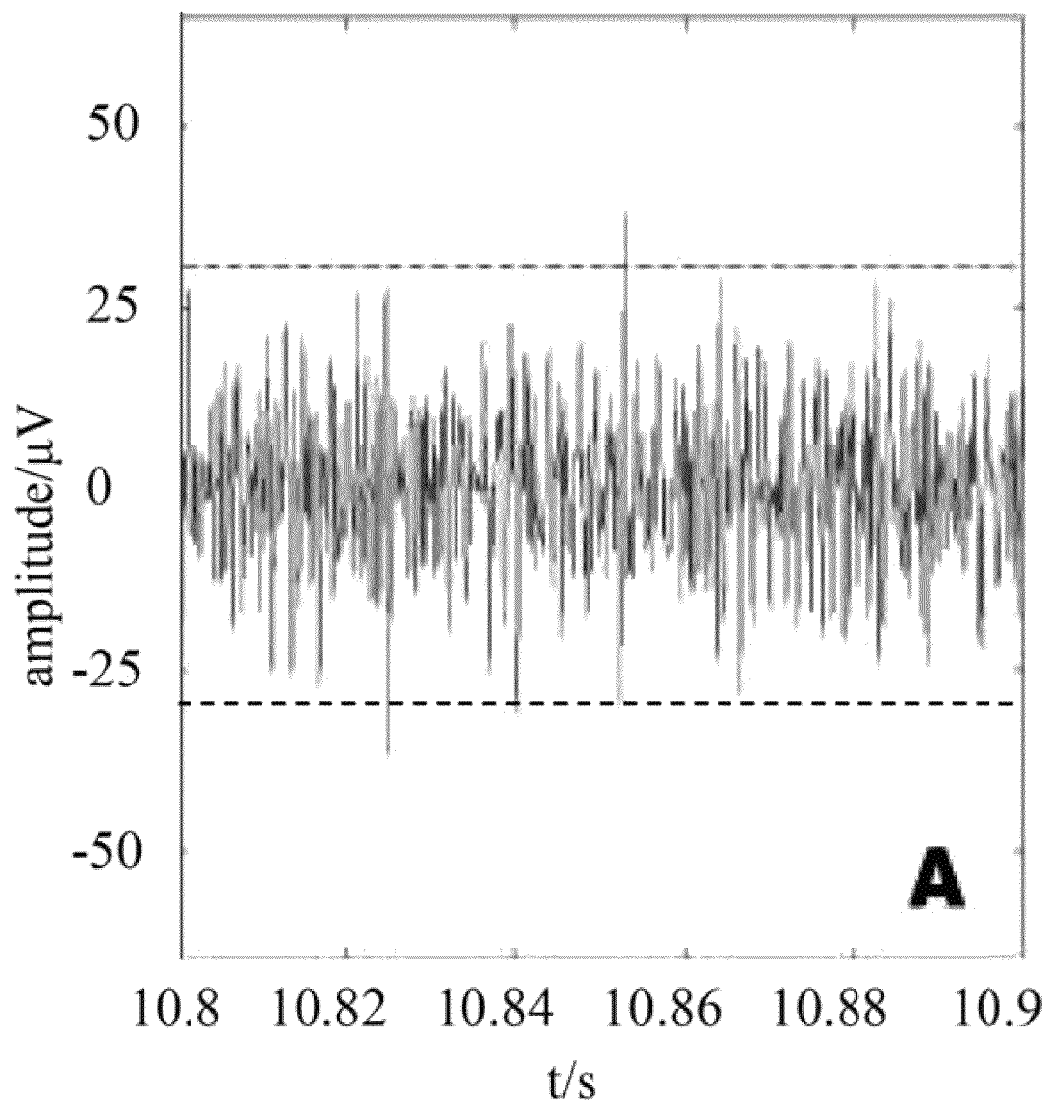
FIGS. 10A-D show graphical summaries of recorded data collected from an exemplary electrode in accordance with the teachings of the present invention.
Figure 10B:
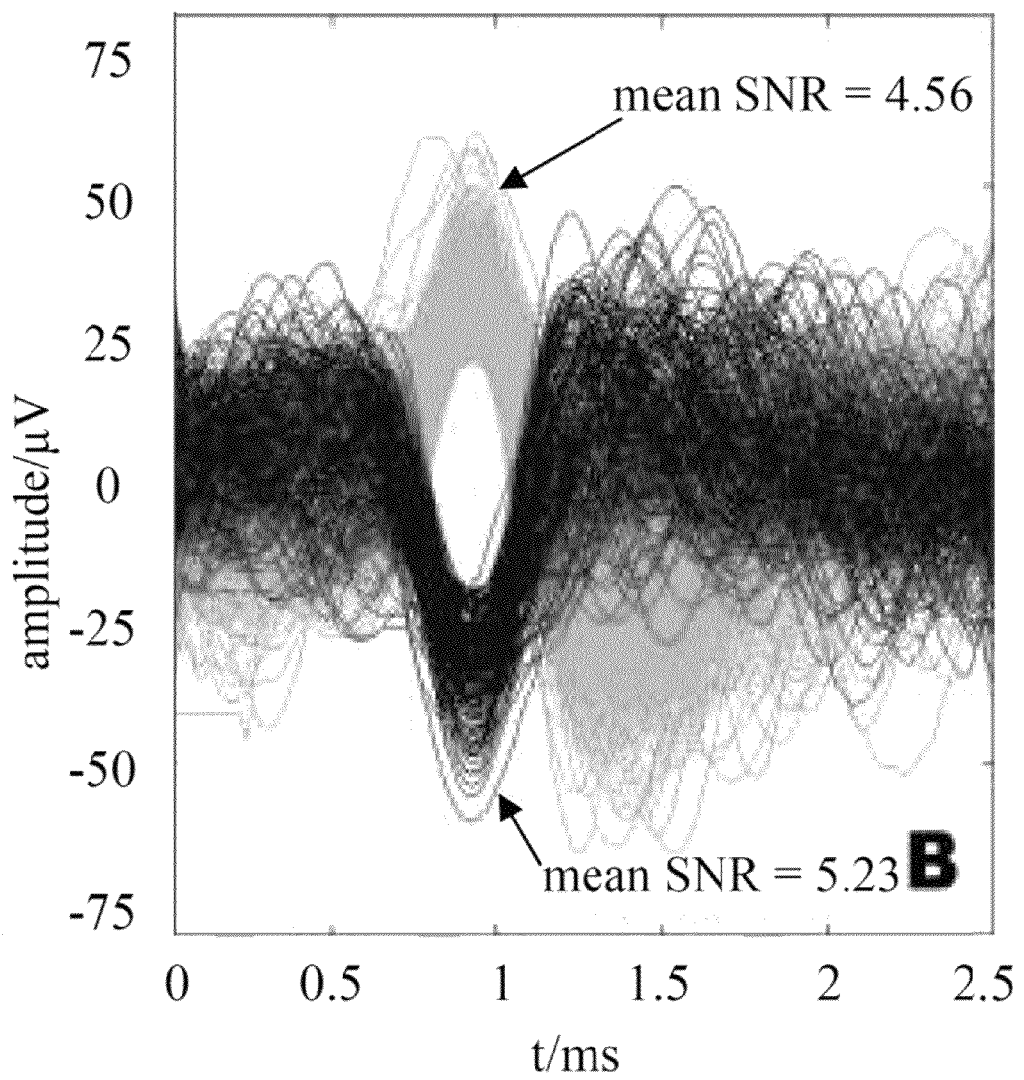
Figure 10C:
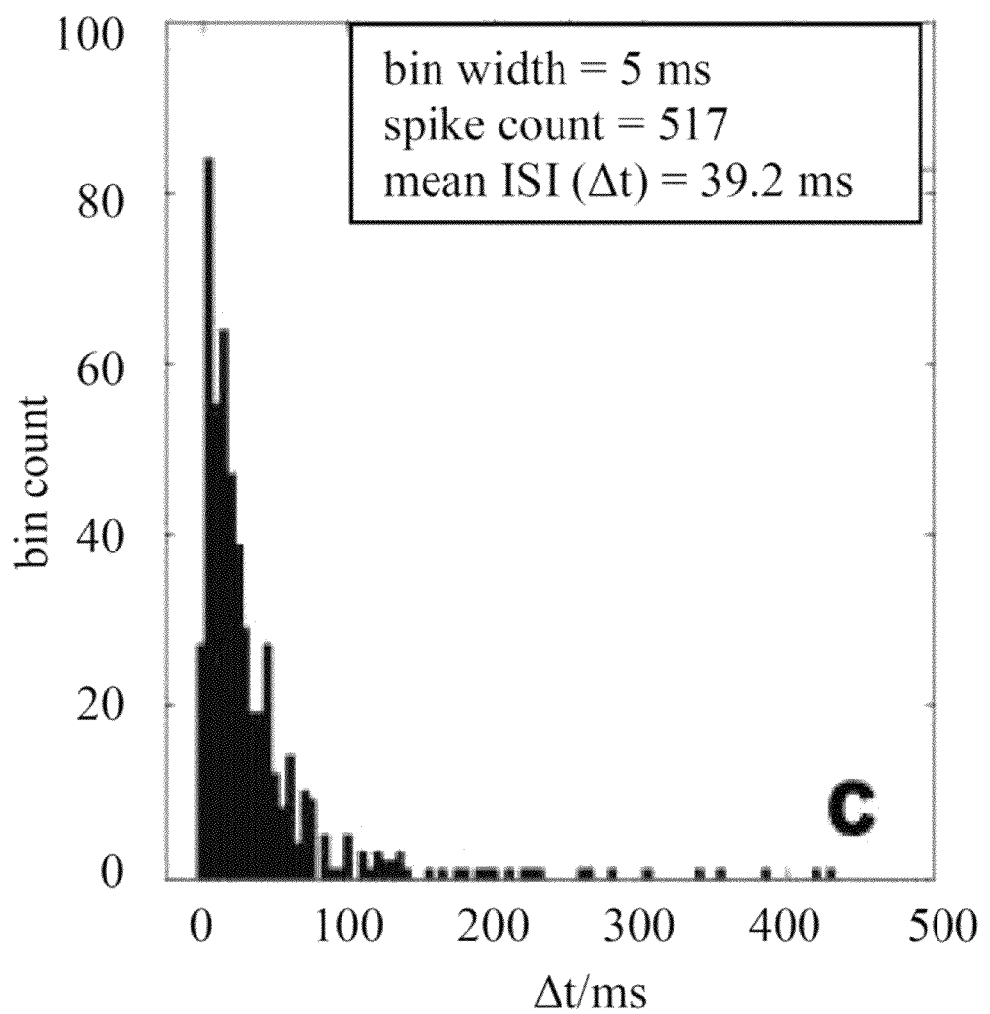
Figure 10D:
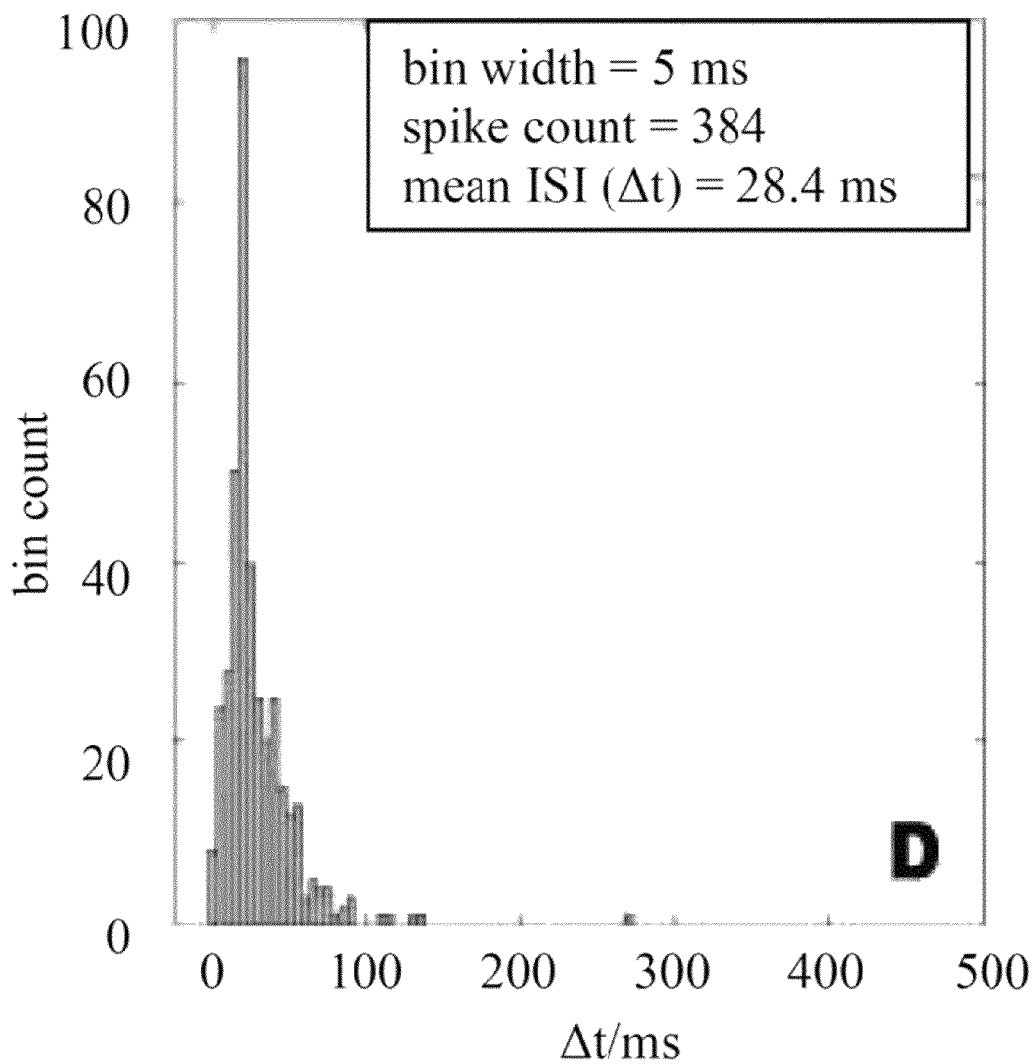

FIG. 10A shows a 100 ms segment of data from electrode 4 with along with the estimated extraction threshold (dotted lines) used in the spike sorting algorithm (see Materials and Methods: Data Collection and Analysis). Two single units, from spontaneous neural activity in S1BF, were discriminated from background activity using OSort (Rutishauser et al., 2006). Peak spike amplitudes recorded from each neuron were approximately 120 $\mu V_{pp}$ (FIG. 10B). The ISI histograms of the extracted single units from electrode 4 are seen in FIGS. 10C and D. The negative spike (downward spike marked by an arrow in FIG. 10B) and positive spike (upward spike marked by an arrow in FIG. 10B) both followed ISI distributions similar to what has been reported in literature (Gerstein and Mandelbrot, 1964; Reich et al., 2000; Softky and Koch, 1993). Both ISI histograms show high counts at short intervals followed by rapid decreases in counts at longer intervals up to approximately 50 ms. The counts at larger intervals >50 ms then taper off into a "long tail" (Gerstein and Mandelbrot, 1964; Reich et al., 2000).

Current neural probe designs are constrained by the need to withstand compressive force during insertion. Widely used silicon-based probes typify the dichotomy between the materials properties needed for insertion and those required for long term viability. Silicon probes are stiff, hard, and of comparatively large diameter allowing for easy insertion. These same qualities lead to the large modulus mismatch between the probe and the surrounding tissue as well as a large initial scar. Subsequent pulsitile micromotion of the brain relative to the probe leads to high stresses at interfacial regions, enhancing glial scar formation (Lee et al., 2005; Subbaroyan et al., 2005). While a number of researchers have attempted to minimize interfacial stresses by using materials with lower moduli, conventional designs are still constrained by the need to push through tissue using compressive force.

The current implantation system accelerates a ferromagnetic tip within a pulsed magnetic field. The tip then pulls along a conductive tether, which is held in tension during acceleration. Upon exiting the magnetic field, the momentum of the probe allows the sharp tip to penetrate neural tissue. The mass of the probe tip is large in proportion to its size. As the electrode penetrates the tissue, the high kinetic energy of the probe tip allows it to drag the tether, overcoming the resistive frictional forces of the surrounding tissues. Energy is imparted to the probe under tension, allowing for the use of materials that are strong under tensile stress. This principal is conceptually analogous to using a thin steel wire to withstand tensile forces equal in magnitude to the compressive forces acting on a thick concrete pillar.

The advantages of using tension based implantation are numerous. Soft flexible polymeric probes with varying sizes and geometries can be implanted over a wide range of depths. Without the size limitations imposed by the need to insert electrodes using conventional methods recording electrodes can be reduced in diameter, thereby reducing the chronic inflammatory response (Seymour and Kipke, 2007). Experimental evidence suggests that macrophages have difficulty adhering to and spreading on polymer fibers ranging between 2.1-5.9 µm in diameter (Bernatchez et al., 1996). Capsule thickness and macrophage density were also significantly reduced on fibers <6 µm in diameter relative to larger fibers implanted in rat subcutaneous dorsum (Sanders et al., 2000). Seymour and Kipke demonstrated that probe size may play a critical role in determining the degree of glial scar formation in the central nervous system (Seymour and Kipke, 2007). In their study, the 5 µm wide lateral edge of a parylene-based probe demonstrated higher neuronal densities and reduced microglial reactivity and protein absorption relative to the thick shank used for implantation. Without the constraints imposed by conventional insertion methods, probe size and geometry can be optimized to minimize long term tissue encapsulation.

The theoretical limits to probe size and geometry given a magnetic implantation system are dependant upon a number of interrelated factors. Probe size, geometry, and mass of ferromagnetic material influences the magnetic properties, kinetic energy potential, and resistance encountered during insertion. Reduction in probe size will reduce the amount of kinetic energy imparted to the probe during acceleration and limit the depth of penetration. Stronger magnetic fields and inductive coil systems with smaller inner coil diameters can be used to impart greater energy to small probes than is possible using the current prototype design. Such systems may be capable of implanting probes that are an order of magnitude smaller than conventional electrodes.

Although agar modeling does demonstrate that insertion depth can be predictably varied based on the strength of the induced magnetic field, further development of the insertion system will require accurate modeling of implantation through tissues with different mechanical properties. While studies have been performed to determine the force required to penetrate neural tissue (Howard et al., 1999; Howard et al., 1989; Molloy et al., 1990), the brain is a viscoelastic structure. Probe velocity and geometry will affect the required penetration force. Accurate modeling of such interactions must therefore be conducted on per-system basis.

The current mathematical model is only a first order approximation of the system as various simplifications and assumption are made to derive the analytical analysis. Some of the factors that are neglected include air resistance, variation of electrode permeability with magnetic field, and termination of magnetic field outside of the driver coil. This first order model is used to give us an idea of how the result numbers will vary, rather than the numbers themselves, due to changes in parameter values. Since this analytical model is only used to determine variations, to achieve comparable results the errors due to the simplifications and assumptions are accounted for in a calibration constant determined in comparisons with measurements. Nonetheless, these equations still provide an estimate of the interactions between the driver coil and electrode.

Hard and stiff probes tend to be brittle. These properties limit the depth of penetration possible without risking fracture. With the new probe design and insertion method presented here, tethered electrodes can be implanted to varying depths by adjusting probe velocity. High implantation velocity has the added benefit of reducing the trauma experienced by surrounding tissues during insertion (Bjornsson et al., 2006; Rennaker et al., 2005). In the current set of experiments, the high velocity probe imparted sufficient kinetic energy to penetrate the meninges. The strength of this tissue layer is reflected in the higher-than-predicted charge voltages needed to achieve ~4 mm penetration depth. Based on the 0.5% agar gel used to model neural tissue, a 320 V charge was tested but was insufficient to penetrate the meninges. Successful implantation was achieved using 480 V and 560 V charges.

The ability to implant probes without removing the meningeal layers simplifies surgical procedures and lessens trauma to cortical neurons. Transdural implantation also lessens the amount of tissue micromotion experienced by the brain. Gilletti and Muthuswamy demonstrated that surface displacement doubled after removal of the dura, going from a mean of 5.8±3.5 µm to 11.4±8.1 µm (Gilletti and Muthuswamy, 2006). Reduced micromotion of neural tissue translates to reduced interfacial stress and glial scar formation. After implantation, local field potentials and discriminable single-unit activity were recorded from S1BF, indicating that surrounding neurons survived the initial insertion. Further investigation is needed to determine the acute and chronic effects of the implantation procedure on the surrounding neural tissue.

The severity of the initial trauma has been implicated as one of the major factors governing implant success (Edell et al., 1992). During insertion, the electrode displaces tissue, severs capillaries, and disrupts extracellular matrix, causing trauma to neurons, astrocytes, and microglia. The damage from insertion results in an acute inflammatory response characterized by activation of the complement cascade, edema, and migration of microglia to the implant site (Polikov et al., 2005). The current device inserts probes along a straight line trajectory, mitigating the slashing phenomena observed with misaligned probes inserted using a stereotactic frame (Edell et al., 1992). While a micromanipulator was utilized to hold the inductive coil in the current investigation, it was not a required element for implantation. Further refinements to this proof-of-concept apparatus will make it possible to construct a hand held portable device. Such a "point-and-shoot" device would greatly reduce the amount of equipment needed for surgery and would improve the ease of implantation.

After insertion, the continued presence of a magnetically mobile tip allows for secondary probe manipulation and positioning. External magnetic fields can be generated to precisely position the electrode into the desired recording field. Secondary magnetic manipulation will also make it possible to navigate around structures such as blood vessels which must be avoided to minimize neural trauma. The magnetic stereotaxis equipment developed by Howard and Grady et al. demonstrates how external magnetic fields are capable of precisely directing the movement of small ferromagnetic "seeds" in neural tissue (Grady et al., 1990b; Howard et al., 1989; McNeil et al., 1995a, b). Originally developed in order to induce local hyperthermia in deep brain structures for the treatment of cancer (Grady et al., 1990a; Grady et al., 1989), magnetic stereotaxis can also be used to manipulate a magnetically tipped catheters such as those described by Gillies et at. (Gillies et al., 1994). The magnetic probes described in this document are conceptually analogous to such catheters and may be manipulated in a similar fashion.

The prototype electrode used in this study is composed of a steel tip soldered to a length of thin copper wire. This design was used only for system verification purposes in an acute surgery. The chronic presence of copper and iron will likely lead to electrochemical degradation of the electrode and local tissue death. Future work to optimize the magnetic implantation system will involve constructing probes from biocompatible materials to allow for chronic neural recordings.

The current implantation system does not preclude the use of the coatings and drug delivery technologies developed for enhanced probe functionality (Kim and Martin, 2006; Shain et al., 2003; Winter et al., 2007; Zhong and Bellamkonda, 2005). Coatings and drug delivery devices developed to improve neural adhesion (He and Bellamkonda, 2005) and prevent glial scar formation (He et al., 2007) may increase the long term efficacy of flexible probes. The wider field of potential tether materials may also allow for the incorporation of drugs and molecules precluded due to current materials constraints. The probe body itself can be used as an encapsulation device for the controlled delivery of pharmaceutical agents. The major materials-based requirement is the incorporation of a ferromagnetic tip. The tip must be strongly attracted to the induced magnetic field in order to impart the kinetic energy needed to penetrate tissue and drag the tether. The number of materials possessing the ferromagnetic strength, merchantability and biocompatibility may pose limitations on future design iterations.

Several potential microfabrication techniques are available for producing small, flexible, magnetically tipped electrodes. A number of researchers have developed methods for incorporating small magnetic particles into curable resins and rubbers (Cho and Ahn, 2003; Farshad and Benine, 2004). The methods employed to produce these composites are diverse and include screen-printing, molding, wet-etching and squeegee-coating techniques (Delille et al., 2006; Lagorce and Allen, 1997; Wang et al., 2004). Alternative techniques include electroplating and bonding of ferromagnetic materials to polymer films (Takeuchi et al., 2004), ion beam implantation of ferromagnetic ions into polymers (Petukhov et al., 2007), and sputtering of magnetic particles onto polymer substrates (Nguyen et al., 2001; Oka et al., 1995). Future work to miniaturize the current prototype system will involve a critical analysis of microfabrication techniques, their advantages, and potential limitations.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

REFERENCES

The following references are incorporated herein by reference in their entirety:

1. Barsoukov E, Macdonald J R. Impedance Spectroscopy: Theory, Experiment, and Applications, 2nd Edition, 2 ed. Wiley-Interscience: Hoboken N.J., 2005.
2. Bernatchez S F, Parks P J, Gibbons D F (1996) Interaction of macrophages with fibrous materials in vitro. Biomaterials 17:2077-2086.
3. Bjornsson C S, Oh S J, Al-Kofahi Y A, Lim Y J, Smith K L, Turner J N, De S, Roysam B, ShaM W, Kim S J (2006) Effects of insertion conditions on tissue strain and vascular damage during neuroprosthetic device insertion. Journal of Neural Engineering 3:196-207.
4. Bresie D A, Andrews J A. Design of a reluctance accelerator. Magnetics, IEEE Transactions on, 1991; 27: 623-7.
5. Cheung K C, Renaud P, Tanila H, Djupsund K (2007) Flexible polyimide microelectrode array for in vivo recordings and current source density analysis. Biosensors & Bioelectronics 22:1783-1790.
6. Cheng D K. Field and Wave Electromagnetics, 2nd ed. Addison-Wesley Publishing Company Reading, 1989.

7. Cho H J, Aim C H. Microscale resin-bonded permanent magnets for magnetic micro-electro-mechanical systems applications. J. Appl. Phys., 2003; 93: 8674-6.
8. Cogan S R. Neural stimulation and recording electrodes. Annu. Rev. Biomed. Eng., 2008; 10: 275-309.
9. Das R, Gandhi D, Krishnan S, Saggere L, Rousche P J (2007) A benchtop system to assess cortical neural interface micromechanics. Ieee Transactions on Biomedical Engineering 54:1089-1096.
10. Delille R, Urdaneta M G, Moseley S J, Smela E. Benchtop polymer MEMS. J. Microelectromech. Syst., 2006; 15: 1108-20.
11. Dobelle W H (2000) Artificial vision for the blind by connecting a television camera to the visual cortex. Asaio Journal 46:3-9.
12. Edell D J, Toi V V, McNeil V M, Clark L D (1992) Factors Influencing the Biocompatibility of Insertable Silicon Microshafts in Cerebral-Cortex. Ieee Transactions on Biomedical Engineering 39:635-643.
13. Farshad M, Benine A. Magnetoactive elastomer composites. Polym. Test, 2004; 23: 347-53.
14. Gerstein G L, Mandelbrot B. Random Walk Models for Spike Activity of Single Neuron. Biophys. J., 1964; 4: 41-&.
15. Gilletti A, Muthuswamy J (2006) Brain micromotion around implants in the rodent somatosensory cortex. Journal of Neural Engineering 3:189-195.
16. Gillies G T, Ritter R C, Broaddus W, Grady M S, Howard M A, McNeil R G. Magnetic Manipulation Instrumentation for Medical Physics Research. Rev. Sci. Instrum., 1994; 65: 533-62.
17. Grady M S, Howard M A, Broaddus W C, Molloy J A, Ritter R C, Quate E G, Gillies G T. Magnetic Stereotaxis—a Technique to Deliver Stereotaxic Hyperthermia. Neurosurgery, 1990a; 27: 1010-6.
18. Grady M S, Howard M A, Molloy J A, Ritter R C, Quate E G, Gillies G T. Nonlinear Magnetic Stereotaxis—3-Dimensional, Invivo Remote Magnetic Manipulation of a Small Object in Canine Brain. Med. Phys., 1990b; 17: 405-15.
19. Grady M S, Howard M A, Molloy J A, Ritter R C, Quate E G, Gillies G T. Preliminary Experimental Investigation of Invivo Magnetic Manipulation—Results and Potential Application in Hyperthermia. Med. Phys., 1989; 16: 263-72.
20. He W, Bellamkonda R V (2005) Nanoscale neuro-integrative coatings for neural implants. Biomaterials 26:2983-2990.
21. He W, McConnell G C, Schneider T M, Bellamkonda R V (2007) A novel anti-inflammatory surface for neural electrodes. Advanced Materials 19:3529-3533.
22. Hirakawa K, Hashizume K, Hayashi T (1981) [Viscoelastic property of human brain—for the analysis of impact injury (author's transl)]. No To Shinkei 33:1057-1065.
23. Hochberg L R, Serruya M D, Friehs G M, Mukand J A, Saleh M, Caplan A H, Branner A, Chen D, Penn R D, Donoghue J P (2006) Neuronal ensemble control of prosthetic devices by a human with tetraplegia. Nature 442: 164-171.
24. Howard M A, Abkes B A, Ollendieck M C, Noh M D, Ritter R C, Gillies G T. Measurement of the force required to move a neurosurgical probe through in vivo human brain tissue. IEEE Trans. Biomed. Eng., 1999; 46: 891-4.
25. Howard M A, Grady M S, Ritter R C, Gillies G T, Quate E G, Molloy J A. Magnetic Movement of a Brain Thermoceptor. Neurosurgery, 1989; 24: 444-8.
26. Ignatius M J, Sawhney N, Gupta A, Thibadeau B M, Monteiro O R, Brown I G (1998) Bioactive surface coatings for nanoscale instruments: Effects on CNS neurons. Journal of Biomedical Materials Research 40:264-274.
27. Kim D H, Martin D C (2006) Sustained release of dexamethasone from hydrophilic matrices using PLGA nanoparticles for neural drug delivery. Biomaterials 27:3031-3037.
28. Lagorce L K, Allen M G. Magnetic and mechanical properties of micromachined strontium ferrite polyimide composites. J. Microelectromech. Syst., 1997; 6: 307-12.
29. Lee H, Bellamkonda R V, Sun W, Levenston M E (2005) Biomechanical analysis of silicon microelectrode-induced strain in the brain. Journal of Neural Engineering 2:81-89.
30. Lee K K, He J P, Singh A, Massia S, Ehteshami G, Kim B, Raupp G (2004) Polyimide-based intracortical neural implant with improved structural stiffness. Journal of Micromechanics and Microengineering 14:32-37.
31. McNeil R G, Ritter R C, Wang B, Lawson M A, Gillies G T, Wika K G, Quate E G, Howard M A, Grady M S. Characteristics of an Improved Magnetic-Implant Guidance-System. IEEE Trans. Biomed. Eng., 1995a; 42: 802-8.
32. McNeil R G, Ritter R C, Wang B, Lawson M A, Gillies G T, Wika K G, Quate E G, Howard M A, Grady M S. Functional Design-Features and Initial Performance-Characteristics of a Magnetic-Implant Guidance-System for Stereotaxic Neurosurgery. IEEE Trans. Biomed. Eng., 1995b; 42: 793-801.
33. Mercanzini A, Cheung K, Buhl D L, Boers M, Maillard A, Colin P, Bensadoun J C, Bertsch A, Renaud P (2008) Demonstration of cortical recording using novel flexible polymer neural probes. Sensors and Actuators a-Physical 143: 90-96.
34. Metz S, Bertsch A, Bertrand D, Renaud P (2004) Flexible polyimide probes with microelectrodes and embedded microfluidic channels for simultaneous drug delivery and multi-channel monitoring of bioelectric activity. Biosensors & Bioelectronics 19:1309-1318.
35. Miller J D. Rowland's Magnetic Analogy to Ohm's Law. Isis, 1975; 66: 230-41.
36. Molloy J A, Ritter R C, Grady M S, Howard M A, Quate E G, Gillies G T. Experimental-Determination of the Force Required for Insertion of a Thermoseed into Deep Brain-Tissues. Ann. Biomed. Eng., 1990; 18: 299-313.
37. Moritz C T, Perlmutter S I and Fetz E E 2008 Direct control of paralysed muscles by cortical neurons Nature 456 639-42.
38. Nguyen L T, Lisfi A, Lodder J C. The effects of metallic underlayers on magnetic properties of obliquely sputtered Co thin films. Joint European Magnetic Symposia (JEMS 01). Elsevier Science By: Grenoble, France, 2001: 374-7.
39. O'Brien D P, Nichols T R, Allen MG (2001) Flexible microelectrode arrays with integrated insertion devices. In: Micro Electro Mechanical Systems, 2001. MEMS 2001. The 14th IEEE International Conference on, pp 216-219.
40. Oka K, Yano N, Furukawa S, Ogasawara I, Yamasaki J, Humphrey F B. Uniaxial Magnetic Fec Thin-Films Sputtered onto Polymer Substrates. 1995 IEEE International Magnetics Conference (INTERMAG 95). Ieee-Inst Electrical Electronics Engineers Inc: San Antonio, Tx, 1995: 3997-9.
41. Otto S R, Brackmann D E, Hitselberger W E, Shannon R V, Kuchta J (2002) Multichannel auditory brainstem implant: update on performance in 61 patients. Journal of Neurosurgery 96:1063-1071.

42. Paxinos G, Watson C (2007) The Rat Brain in Stereotaxic Coordinates. booksgooglecom.
43. Petukhov V Y, Khabibullina N R, Ibragimova M I, Bukharaev A A, Biziaev D A, Zheglov E P, Gurnarov G G, Muller R. Magnetic properties of thin metal-polymer films prepared by high-dose ion-beam implantation of iron and cobalt ions into polyethylene terephthalate. Appl. Magn. Reson., 2007; 32: 345-61.
44. Polikov V S, Tresco P A, Reichert W M (2005) Response of brain tissue to chronically implanted neural electrodes. Journal of Neuroscience Methods 148:1-18.
45. Ramo S, Whinnery J R, Duzer T V. Fields and Waves in Communication Electronics, 3rd ed. John Wiley & Sons, Inc.: Hoboken, 1965.
46. Reich D S, Mechler F, Purpura K P, Victor J D. Interspike intervals, receptive fields, and information encoding in primary visual cortex. J. Neurosci., 2000; 20: 1964-74.
47. Rennaker R L, Street S, Ruyle A M, Sloan A M (2005) A comparison of chronic multi-channel cortical implantation techniques: manual versus mechanical insertion. Journal of Neuroscience Methods 142:169-176.
48. Richardson-Burns S M, Hendricks J L, Martin D C (2007a) Electrochemical polymerization of conducting polymers in living neural tissue. Journal of Neural Engineering 4:L6-L13.
49. Richardson-Burns S M, Hendricks J L, Foster B, Povlich L K, Kim D H, Martin D C (2007b) Polymerization of the conducting polymer poly(3,4-ethylenedioxythiophene) (PEDOT) around living neural cells. Biomaterials 28:1539-1552.
50. Rousche P J, Pellinen D S, Pivin D P, Williams J C, Vetter R J, Kipke D R (2001) Flexible polyimide-based intracortical electrode arrays with bioactive capability. Ieee Transactions on Biomedical Engineering 48:361-371.
51. Rutishauser U, Schuman E M, Mamelak A N (2006) Online detection and sorting of extracellularly recorded action potentials in human medial temporal lobe recordings, in vivo. Journal of Neuroscience Methods 154:204-224.
52. Sanders J E, Stiles C E, Hayes C L (2000) Tissue response to single-polymer fibers of varying diameters: Evaluation of fibrous encapsulation and macrophage density. Journal of Biomedical Materials Research 52:231-23
53. Schmidt E M, Bak M J, Hambrecht F T, Kufta C V, Orourke D K, Vallabhanath P (1996) Feasibility of a visual prosthesis for the blind based on intracortical microstimulation of the visual cortex. Brain 119:507-522.
54. Sears F W. Electricity and Magnetism. Wesley Publishing: Cambridge, 1954.
55. Seymour J P, Kipke D R (2007) Neural probe design for reduced tissue encapsulation in CNS. Biomaterials 28:3594-3607.
56. Shain W, Spataro L, Dilgen J, Haverstick K, Retterer S, Isaacson M, Saltzman M, Turner J N (2003) Controlling cellular reactive responses around neural prosthetic devices using peripheral and local intervention strategies. Ieee Transactions on Neural Systems and Rehabilitation Engineering 11:186-188.
57. Sharp A A, Panchawagh H V, Ortega A, Artale R, Richardson-Burns S, Finch D S, Gall K, Mahajan R L, Restrepo D (2006) Toward a self-deploying shape memory polymer neuronal electrode. Journal of Neural Engineering 3:L23-L30.
58. Singh A, Ehteshami G, Massia S, He J P, Storer R G, Raupp G (2003) Glial cell and fibroblast cytotoxicity study on plasma-deposited diamond-like carbon coatings. Biomaterials 24:5083-5089.
59. Softky W R, Koch C. The Highly Irregular Firing of Cortical-Cells Is Inconsistent with Temporal Integration of Random Epsps. J. Neurosci., 1993; 13: 334-50.
60. Stieglitz T, Gross M (2002) Flexible BIOMEMS with electrode arrangements on front and back side as key component in neural prostheses and biohybrid systems. Sensors and Actuators B-Chemical 83:8-14.
61. Strumwasser F (1958) Long-Term Recording from Single Neurons in Brain of Unrestrained Mammals. Science 127: 469-470.
62. Subbaroyan J, Martin D C, Kipke D R (2005) A finite-element model of the mechanical effects of implantable microelectrodes in the cerebral cortex. Journal of Neural Engineering 2:103-113.
63. Swindle MM, et al. (2002) Laboratory Animal Medicine, 2nd Edition: Academic Press: An imprint of Elsevier Science.
64. Szarowski D H, Andersen M D, Retterer S, Spence A J, Isaacson M, Craighead H G, Turner J N, Shain W. Brain responses to micro-machined silicon devices. Brain Res., 2003; 983: 23-35.
65. Takeuchi S, Suzuki T, Mabuchi K, Fujita H (2004) 3D flexible multichannel neural probe array. Journal of Micromechanics and Microengineering 14:104-107.
66. Takeuchi S, Ziegler D, Yoshida Y, Mabuchi K, Suzuki T (2005) Parylene flexible neural probes integrated with microfluidic channels. Lab on a Chip 5:519-523.
67. Wang W S, Yao Z M, Chen J C, Fang J. Composite elastic magnet films with hard magnetic feature. J. Micromech. Microeng., 2004; 14: 1321-7.
68. Weppelmann E R, Field J, Swain M V (1993) Observation, Analysis, and Simulation of the Hysteresis of Silicon Using Ultra-Micro-Indentation with Spherical Indenters. Journal of Materials Research 8:830-840.
69. Williams J C, Hippensteel J A, Dilgen J, Shain W, Kipke D R. Complex impedance spectroscopy for monitoring tissue responses to inserted neural implants. Journal of Neural Engineering, 2007; 4: 410-23.
70. Williams J C, Rennaker R L, Kipke D R (1999) Long-term neural recording characteristics of wire microelectrode arrays implanted in cerebral cortex. Brain Research Protocols 4:303-313.
71. Winter J O, Cogan S F, Rizzo J F (2007) Neurotrophin-eluting hydrogel coatings for neural stimulating electrodes. Journal of Biomedical Materials Research Part B-Applied Biomaterials 81B:551-563.
72. Zhong Y H, Bellamkonda R V (2005) Controlled release of anti-inflammatory agent alpha-MSH from neural implants. Journal of Controlled Release 106:309-318.
73. Ziegler D, Suzuki T, Takeuchi S (2006) Fabrication of flexible neural probes with built-in microfluidic channels by thermal bonding of Parylene. Journal of Microelectromechanical Systems 15:1477-1482.

What is claimed is:

1. An apparatus for insertion of a probe into tissue, comprising:
   a probe having two ends, a length between two ends, a tip at one end, and a maximum diameter, said probe being insertable into the tissue in a direction;
   a flexible electrical conductor attached to the other end of said probe;
   an electromagnet comprising a coil defining an open interior having a magnetic field, the electromagnet disposed such that the tip passes through at least a portion of the open interior in the direction when the electromagnet is energized;

a tube having an inner diameter greater than the maximum diameter of said probe, said tube being adapted and configured guide the direction of said tip after said tip passes through the portion of the open interior and wherein the electromagnet drives the two ends of the probe out of the tube.

2. The apparatus of claim 1 wherein said tip comprises a ferromagnetic material.

3. The apparatus of claim 1 wherein said electromagnet includes a plurality of coils, and said tip is placed within the coils.

4. The apparatus of claim 1 wherein the tip is conically shaped.

5. The apparatus of claim 1 wherein said probe has an outer shape adapted and configured for penetration of tissue.

6. The apparatus of claim 1 wherein said tube comprises glass.

7. The apparatus of claim 1 which further comprises a magnet for maintaining the position of said tip within said tube prior to insertion.

8. The apparatus of claim 1 wherein the maximum diameter is less than about six tenths of a millimeter.

9. The apparatus of claim 1 wherein a portion of said tube is located centrally within said coil.

10. The apparatus of claim 1 wherein said tube has a central axis, said coil has a central axis, and the axes are aligned.

11. The apparatus of claim 1 which further comprises a magnet having a constant magnetic field, said magnet being located so as to maintain the position of said probe relative to said electromagnet.

12. A system for inserting a probe into tissue, comprising:
a source of electric power;
an electromagnetic coil defining an open interior, the electromagnetic coil receiving power from said source and creating a transient magnetic field in response thereto;
a probe having two ends and a tip at a first end of the two ends, the probe capable of being propelled through the open interior by the transient magnetic field;
an electrical conductor attached to said probe; and
an ejection tube located proximate to said coil, said tube being adapted and configured to guide said tip;
wherein application of power from said source to said coil creates the transient magnetic field which induces a magnetomotive force on said probe to propel said two ends of the probe out of said tube.

13. The system of claim 12 which further comprises a magnet having a constant magnetic field, said magnet being located so as to maintain the position of said probe within said tube.

14. The system of claim 12 wherein said source includes a capacitor.

15. The system of claim 14 wherein said source includes a bank of capacitors.

16. The system of claim 12 wherein the first end adapted and configured for entry into the tissue, and a tether is attached to a second end of the two ends of said probe.

17. The system of claim 12 wherein a portion of said tube is located centrally within said coil.

18. The system of claim 12 wherein said tube has a central axis, said coil has a central axis, and the axes are aligned.

19. The system of claim 16 wherein said tether comprises the electrical conductor.

20. An apparatus for insertion of a probe into tissue, comprising:
a probe having two ends, a length between two ends, a tip at one end, and a maximum diameter, said probe being insertable into the tissue in a direction;
a flexible electrical conductor attached to the other end of said probe;
a tube having an inner diameter greater than the maximum diameter of said probe, said tube being adapted and configured guide the direction of said tip
an electromagnet having a magnetic field, the electromagnet positioned to cause the magnetic field to interact with the probe to drive the two ends of the probe out of the tube.

* * * * *